(12) United States Patent
Asahina

(10) Patent No.: US 10,123,771 B2
(45) Date of Patent: Nov. 13, 2018

(54) ULTRASOUND MEDICAL APPARATUS AND ULTRASOUND DIAGNOSIS APPARATUS

(71) Applicant: Toshiba Medical Systems Corporation, Otawara-shi (JP)

(72) Inventor: Hiroshi Asahina, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 896 days.

(21) Appl. No.: 14/474,830

(22) Filed: Sep. 2, 2014

(65) Prior Publication Data

US 2014/0371596 A1 Dec. 18, 2014

Related U.S. Application Data

(63) Continuation of application No. PCT/JP2013/077174, filed on Oct. 4, 2013.

(30) Foreign Application Priority Data

Oct. 4, 2012 (JP) ................................ 2012-222587

(51) Int. Cl.
*A61B 8/00* (2006.01)
*A61B 8/12* (2006.01)
(Continued)

(52) U.S. Cl.
CPC .......... *A61B 8/4444* (2013.01); *A61B 8/0883* (2013.01); *A61B 8/12* (2013.01);
(Continued)

(58) Field of Classification Search
CPC .. A61B 8/00; A61B 18/00; A61B 8/12; A61B 8/483; A61B 8/56; A61B 8/0883; A61B 8/445; A61B 8/14; A61B 8/488
See application file for complete search history.

(56) References Cited

U.S. PATENT DOCUMENTS

2003/0092964 A1   5/2003  Kim et al.
2007/0167825 A1*  7/2007  Lee .......................... A61B 8/12
                                                          600/463

(Continued)

FOREIGN PATENT DOCUMENTS

CN       201441450 U    4/2010
CN       102065775 A    5/2011
(Continued)

OTHER PUBLICATIONS

International Search Report dated Nov. 5, 2013 for PCT/JP2013/077174 filed on Oct. 4, 2013 with English Translation.

(Continued)

*Primary Examiner* — Joel Lamprecht
(74) *Attorney, Agent, or Firm* — Oblon, McClelland, Maier & Neustadt, L.L.P.

(57) ABSTRACT

Ultrasound medical apparatus and ultrasound diagnosis apparatus are provided capable of indwelling in the observation object at a desired position of the inner cavity of the subject.

The ultrasound medical apparatus according to the embodiments include a sheath, a capsule body unit, and a fixation mechanism. The sheath is inserted into the inner cavity of a subject, having an outer peripheral surface that contacts the inner wall surface of the inner cavity of the subject with a liquid filled inside thereof. The capsule body unit is inserted into the sheath, and configured to store an ultrasound transducer that transmits and receives ultrasound waves to and from the subject. The fixation mechanism is provided in at least one of the capsule body unit and the sheath, to fixedly arrange the capsule body unit at a desired position in the sheath.

14 Claims, 47 Drawing Sheets

(51) Int. Cl.
  *A61B 8/08* (2006.01)
  *A61B 8/14* (2006.01)
  *G01S 15/89* (2006.01)
  *G01S 7/52* (2006.01)
(52) U.S. Cl.
  CPC ............... *A61B 8/14* (2013.01); *A61B 8/445* (2013.01); *A61B 8/483* (2013.01); *A61B 8/488* (2013.01); *A61B 8/56* (2013.01); *G01S 7/52079* (2013.01); *G01S 15/8915* (2013.01)

(56) References Cited

U.S. PATENT DOCUMENTS

| 2008/0194912 A1* | 8/2008 | Trovato | A61B 1/00055 600/118 |
| 2009/0270736 A1* | 10/2009 | Miyamoto | A61B 8/12 600/462 |
| 2011/0118601 A1 | 5/2011 | Barnes et al. | |
| 2012/0004506 A1* | 1/2012 | Tearney | A61B 1/00082 600/116 |
| 2012/0150024 A1 | 6/2012 | Amit et al. | |

FOREIGN PATENT DOCUMENTS

| CN | 102525596 A | 7/2012 |
| JP | 63-288142 A | 11/1988 |
| JP | 2003-135388 A | 5/2003 |
| JP | 2004-440 A | 1/2004 |
| JP | 2004-222998 A | 8/2004 |

OTHER PUBLICATIONS

Jan N. Hilberath, et al., "Safety of Transesophageal Echocardiography", Journal of the American Society of Echocardiography, 2010, p. 1115-1127.

A. Vegas, et al., "Real-Time Three-Dimensional Transesophageal Echocardiography", Springer Science+Business Media, 2012, p. 26-51.

Combined Chinese Office Action and Search Report dated Sep. 25, 2015 in Patent Application No. 201380021433.9 (with English Translation of Categories of Cited Documents).

* cited by examiner

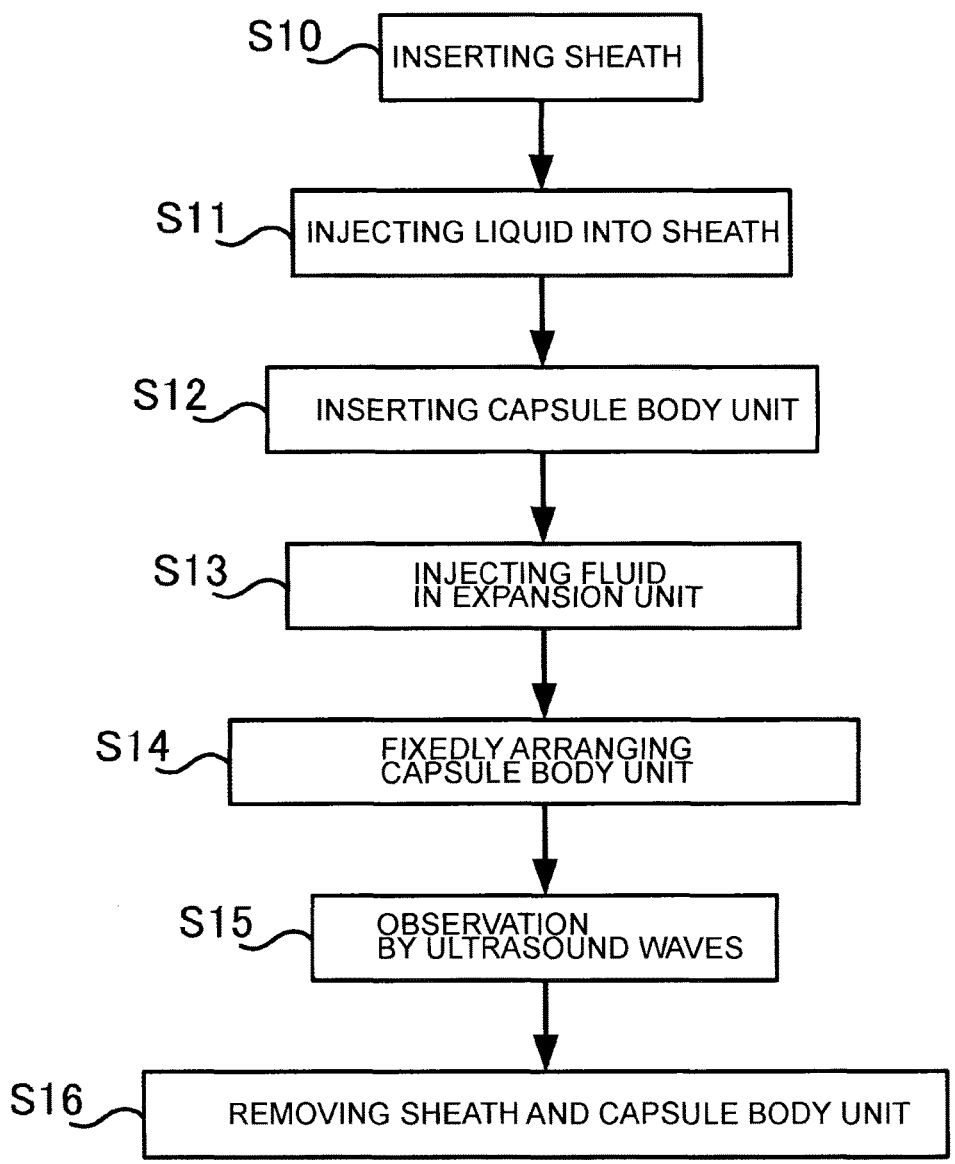

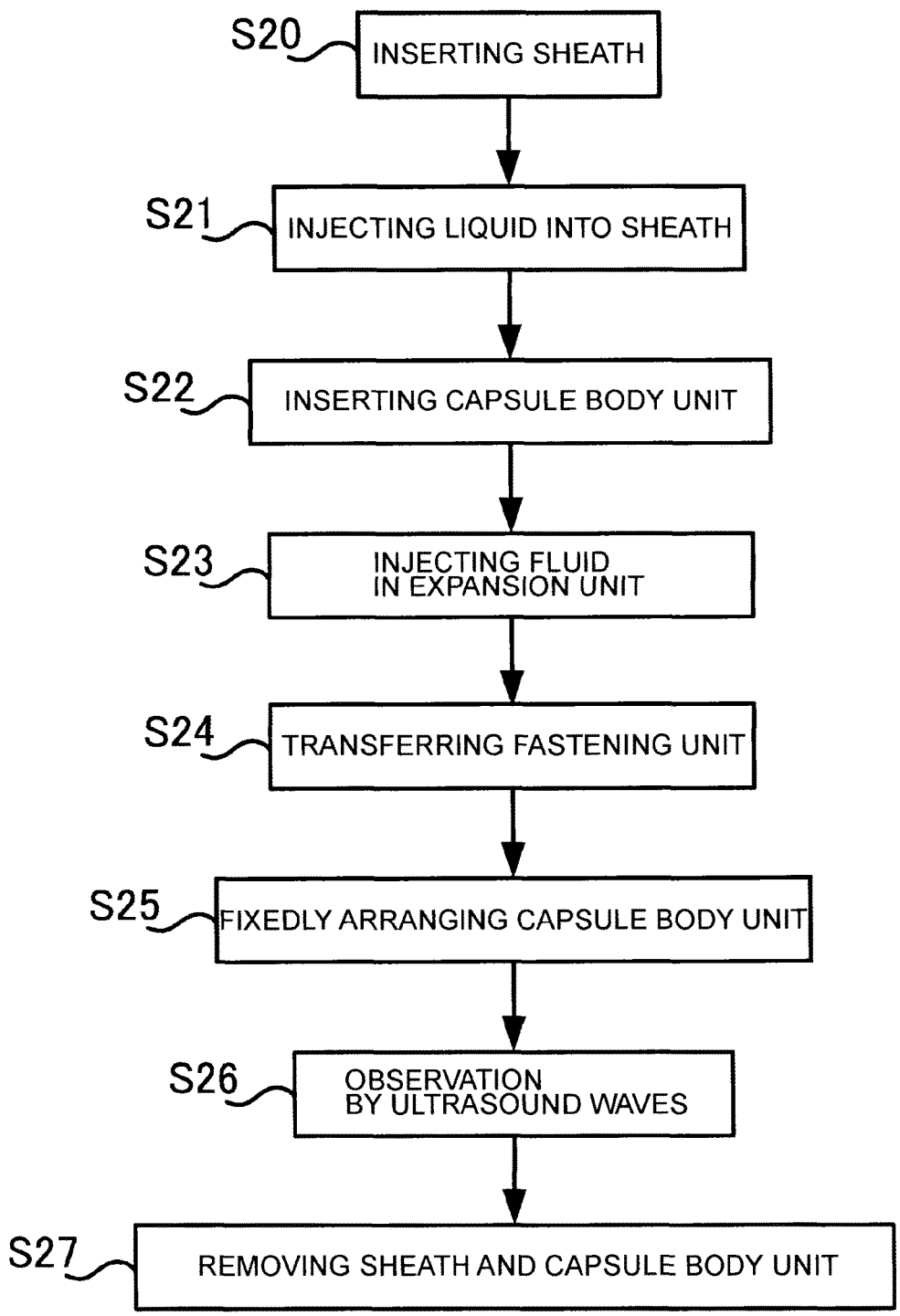

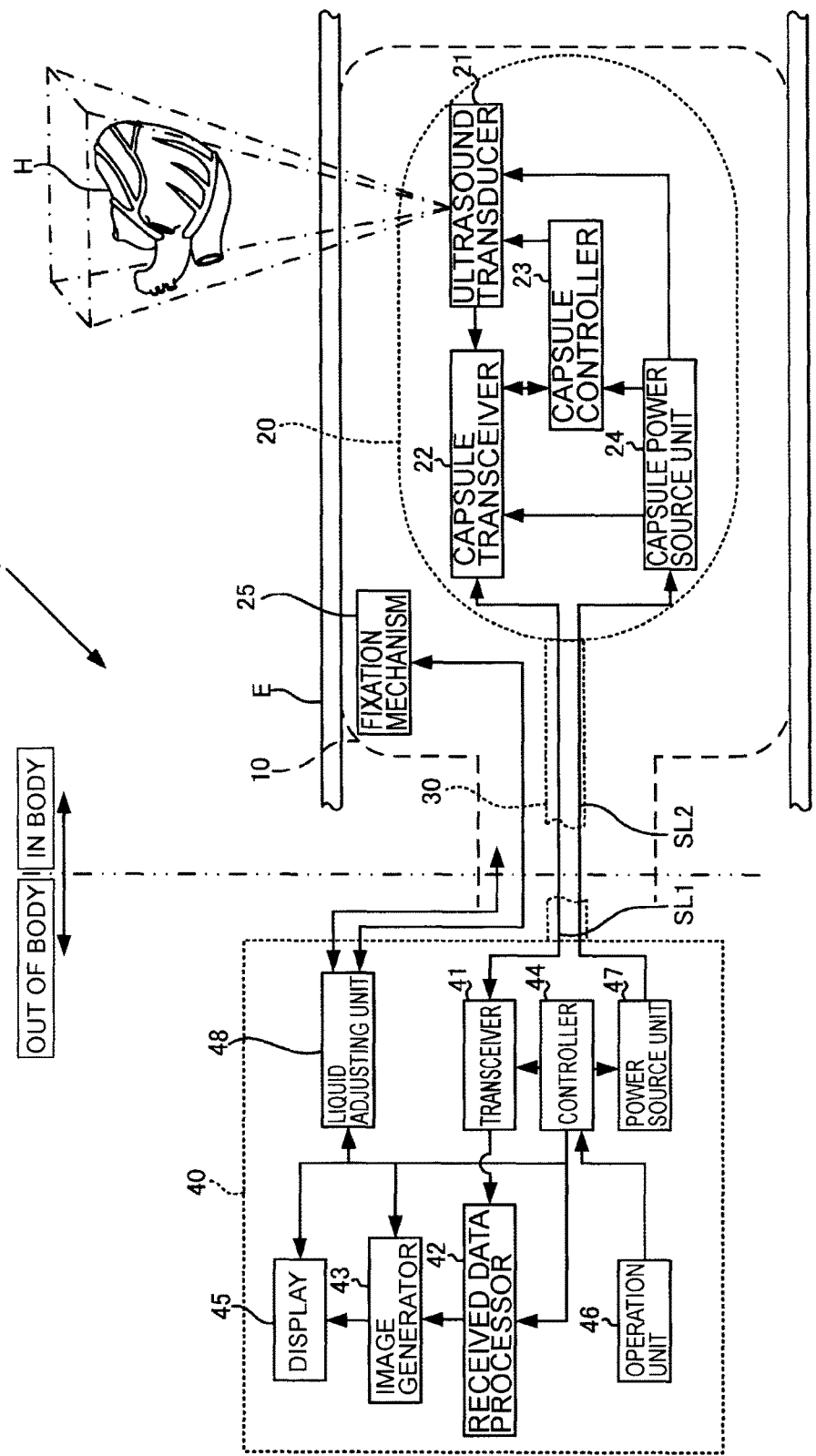

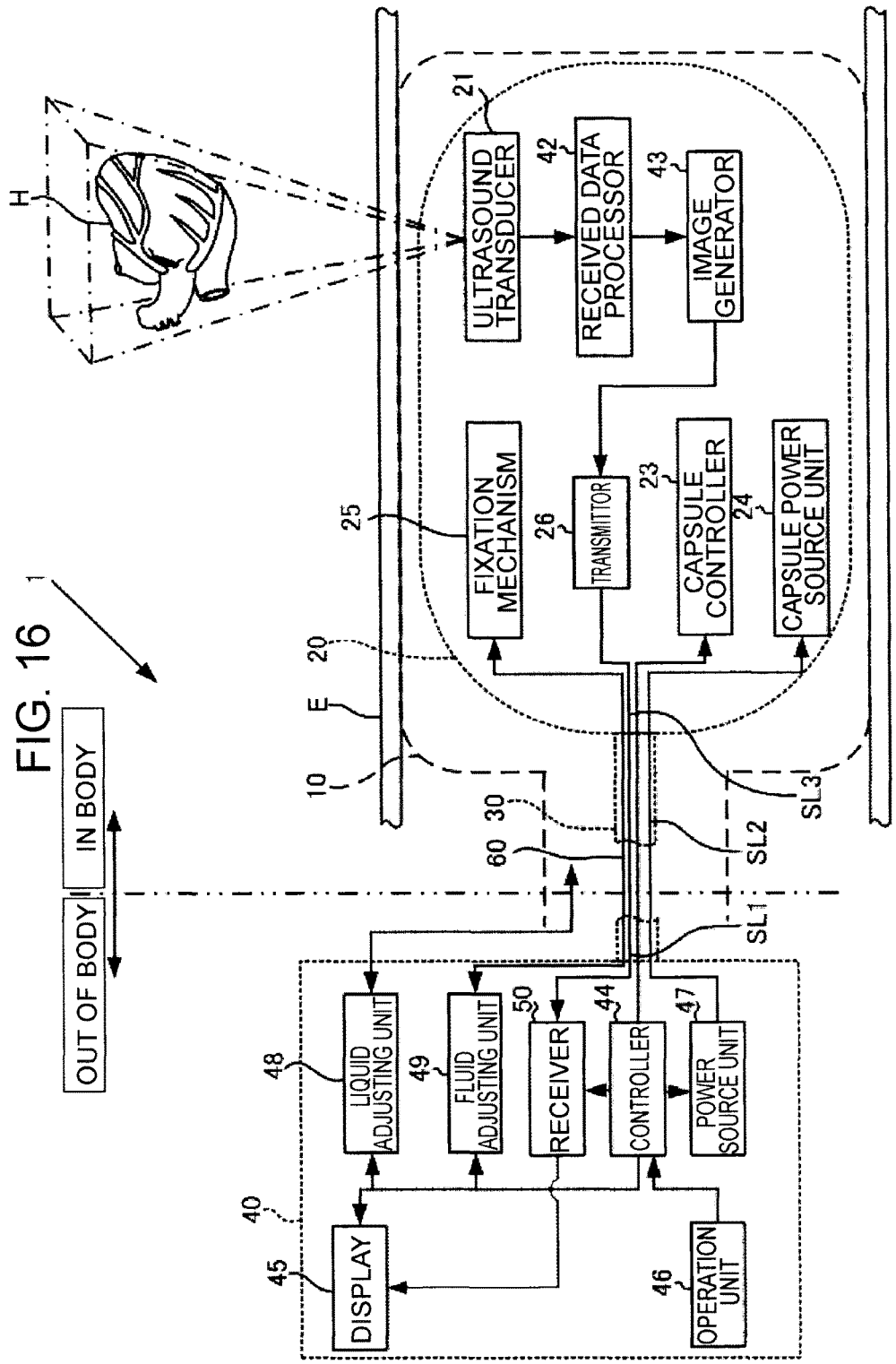

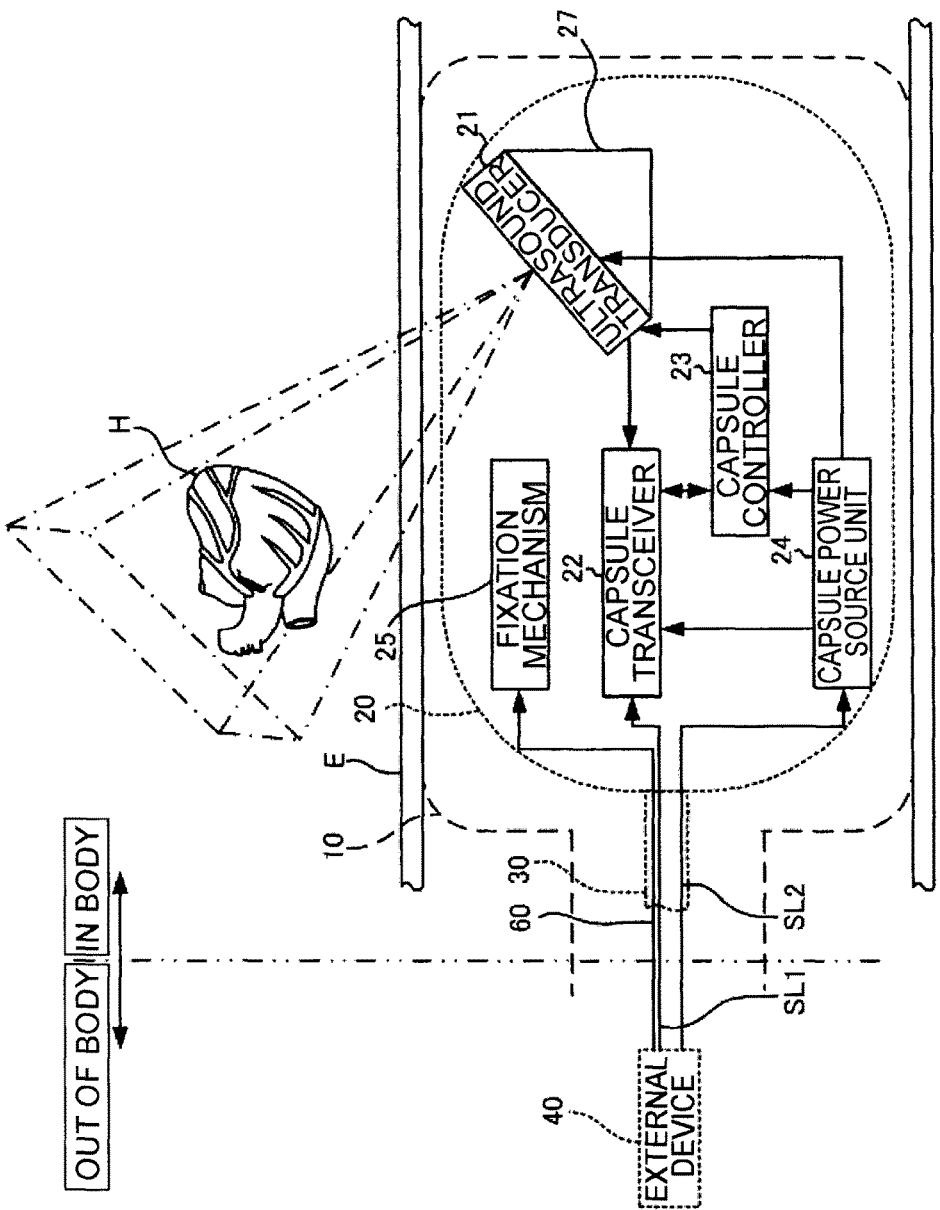

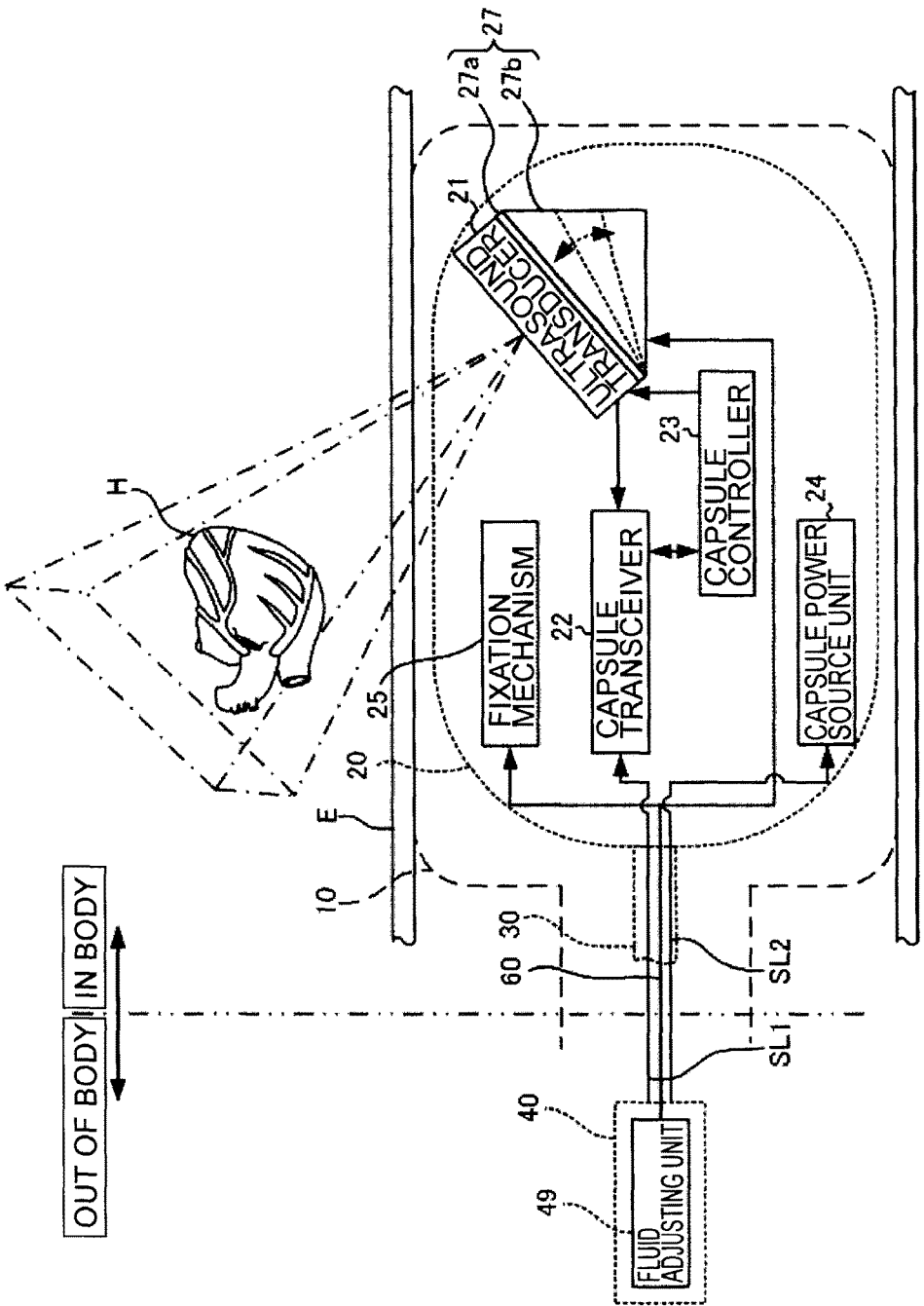

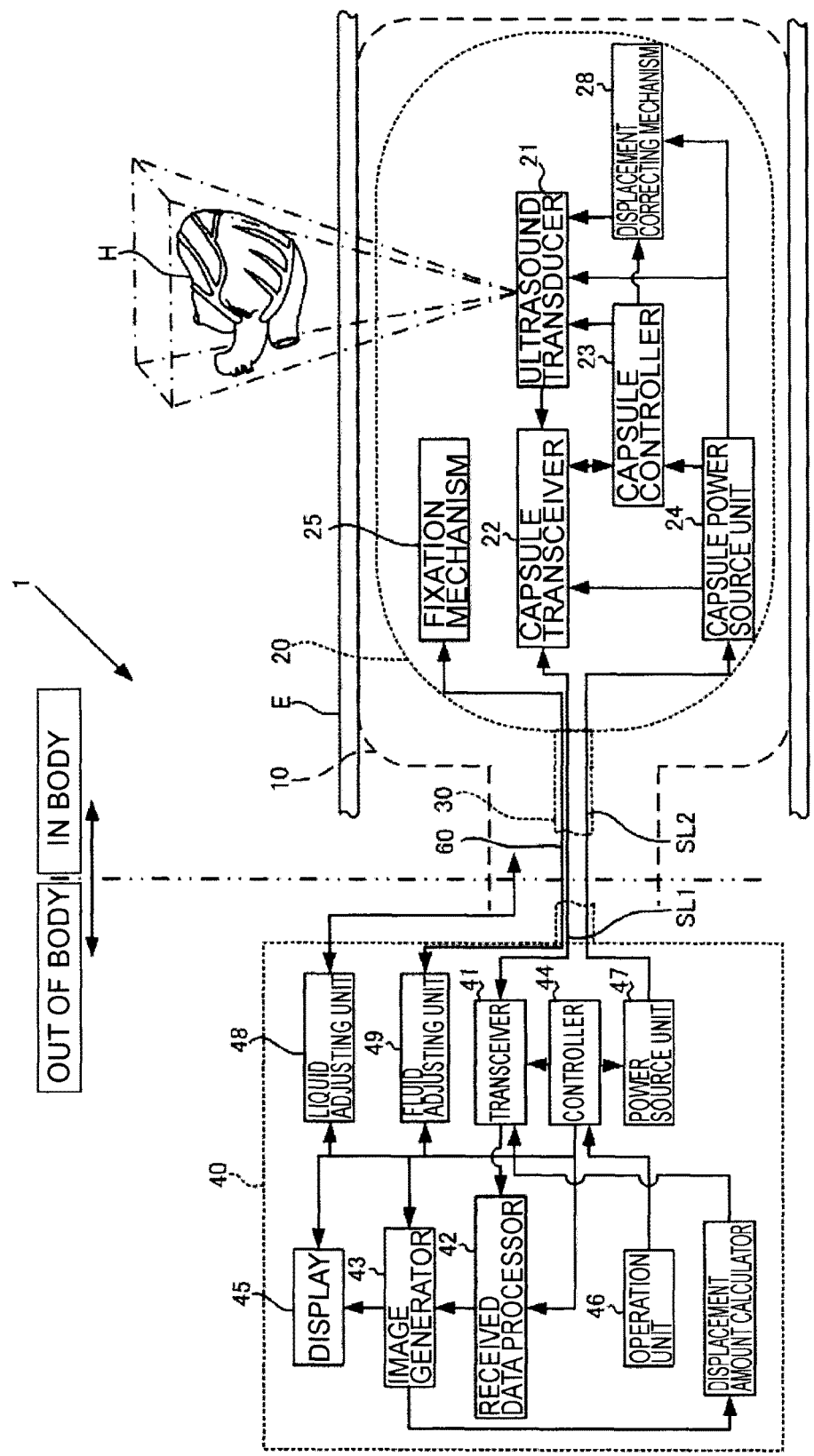

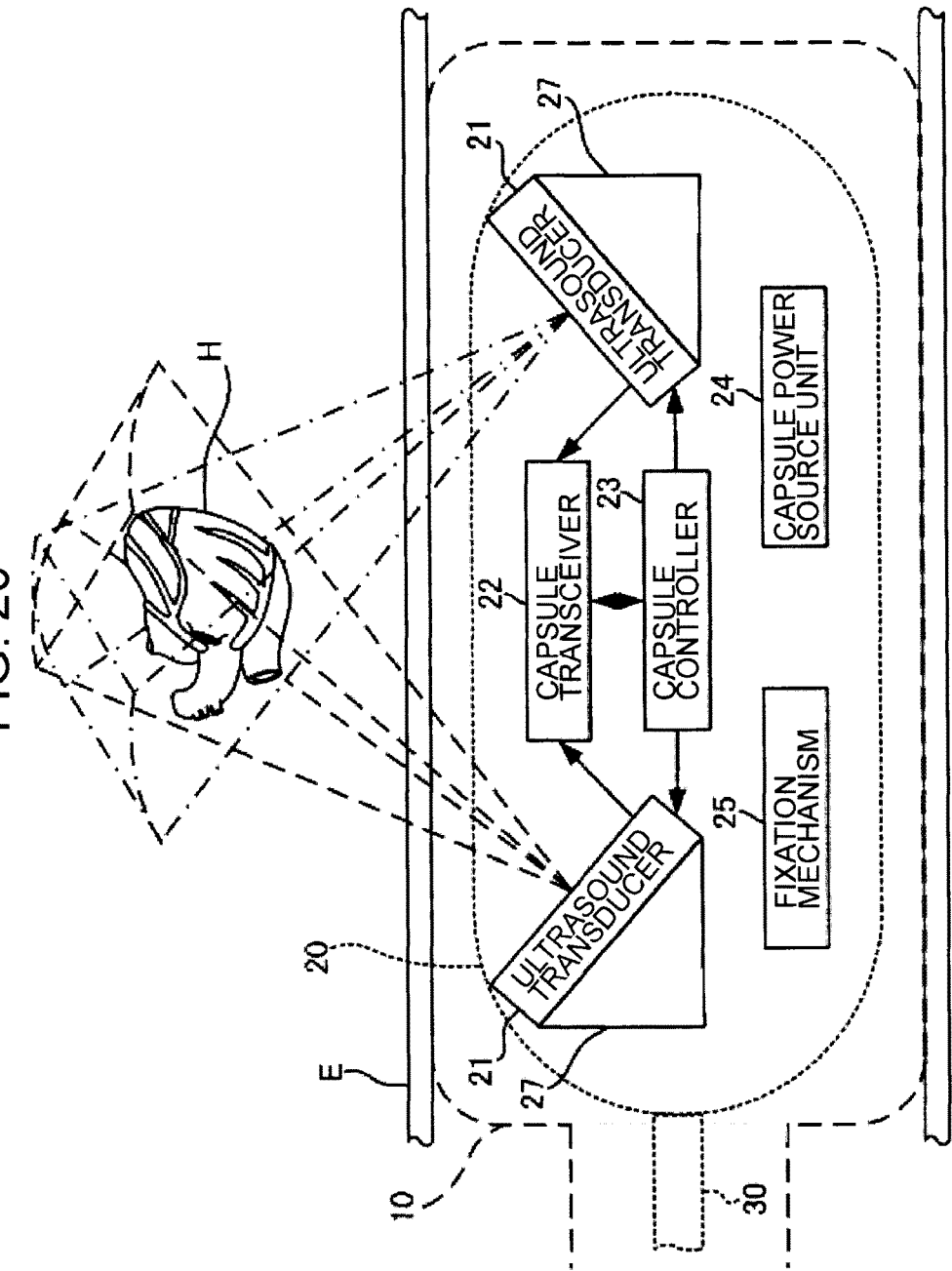

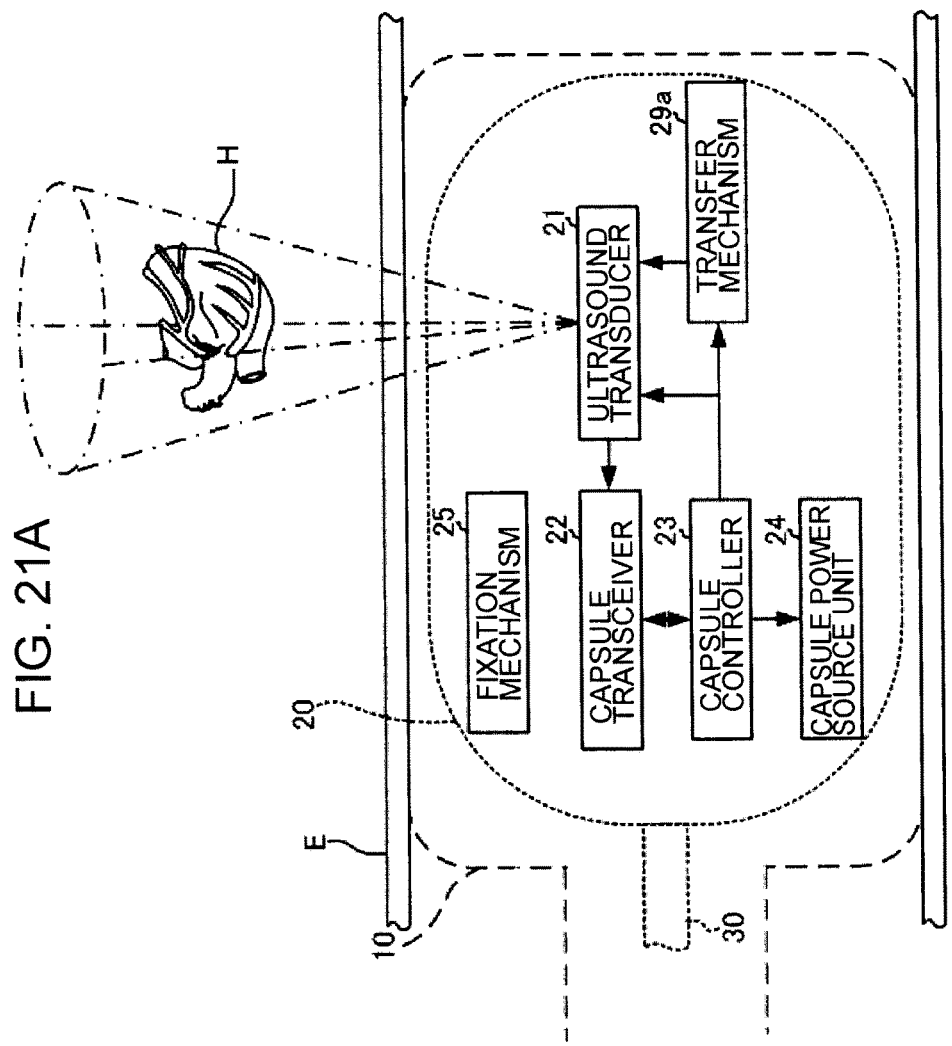

ULTRASOUND MEDICAL APPARATUS AND ULTRASOUND DIAGNOSIS APPARATUS

CROSS-REFERENCE TO RELATED APPLICATION

This application is based upon and claims the benefit of priority from Japanese Patent Applications No. 2012-222587 filed on Oct. 4, 2012; the entire contents of which are incorporated herein by reference.

FIELD

The embodiments of the present invention relate to an ultrasound medical apparatus and an ultrasound diagnosis apparatus.

BACKGROUND

Ultrasound diagnosis apparatuses scan the inside of a subject with ultrasound waves via an ultrasound probe for imaging the inside of the subject based on echo signals generated from the reflected ultrasound waves.

An example of the ultrasound probe used for ultrasound diagnosis apparatuses is a Transesophageal Echocardiography (TEE) probe. A TEE probe is orally inserted into the upper gastrointestinal tract of, for example, the esophagus, the stomach, or the like, to be used for imaging the heart, or the like, via the esophagus wall and the stomach wall. The TEE probe is formed by an insertion part to be inserted into the upper gastrointestinal tract, a guiding hollow tube to be inserted into the esophagus, a bending part with an operable bending angle, which connects the guiding hollow tube to the insertion part, an operation unit that operates the bending angle of the bending part, and a connector part to be connected to the body part of the ultrasound diagnosis apparatus. The insertion part of the TEE probe includes an ultrasound transducer disposed at a front end thereof. It is possible to acquire images of the heart, or the like, without being affected by the bones and subcutaneous fat by imaging the heart, or the like, from the inner cavity of the subject using the TEE probe.

However, the operation of the TEE probe is complicated. Accordingly, an operator requires proficiency in order to observe a target site. For example, in the case of observing the heart, or the like, it is necessary to carry out positioning of the insertion part by adjusting the degree of insertion of an introduction tube of the TEE probe so that ultrasound waves are applied to the section of the heart, or the like, to be observed, then operating the bending angle of the bending part. If the operator makes a mistake during insertion of the introduction tube or the operation of the bending angle of the bending part, bleeding and rupture may occur in the esophagus wall or the stomach wall. Moreover, in the case of monitoring the heart, or the like, over time during heart operations, or the like, the insertion part of the TEE probe may be indwelled in a desired position for a certain period. In this case, conventionally, the operator can maintain the position of the insertion part only by manually holding the TEE probe. Further, this becomes a heavy burden as the probe is held in the throat of the subject with the introduction tube left inserted. In other words, it is difficult for the conventional TEE probe to indwell in the observation object (the heart, or the like), with no structure suitable for indwelling for an extended period of time.

BRIEF DESCRIPTION OF THE DRAWINGS

FIG. 7 is a flowchart illustrating the operation of the ultrasound diagnosis apparatus according to the first embodiment.

FIG. 10 is a flowchart illustrating the operation of the ultrasound diagnosis apparatus according to the second embodiment.

FIG. 11 is a block diagram illustrating the outline of the ultrasound diagnosis apparatus according to a third embodiment.

FIG. 16 is a block diagram illustrating another example of the ultrasound diagnosis apparatus according to the modified example 2.

FIG. 17 is a block diagram illustrating the outline of the capsule body unit according to a modified example 3.

FIG. 18 is a block diagram illustrating another example of the capsule body unit according to the modified example 3.

FIG. 19 is a block diagram illustrating the outline of the ultrasound diagnosis apparatus according to a modified example 4.

FIG. 20 is a block diagram illustrating the outline of the capsule body unit according to a modified example 5.

FIG. 21A is a block diagram illustrating another example of the capsule body unit according to the modified example 5.

DETAILED DESCRIPTION

The embodiments have been created for solving the abovementioned problems, with the object intended to provide an ultrasound medical apparatus and an ultrasound diagnosis apparatus capable of indwelling in the observation object at a desired position of the inner cavity of the subject.

The ultrasound medical apparatus according to the embodiments include a sheath, a capsule body unit, and a fixation mechanism. The sheath is inserted into the inner cavity of a subject, having an outer peripheral surface that contacts the inner wall surface of the inner cavity of the subject with a liquid filled inside thereof.

The capsule body unit is inserted into the sheath, and configured to store an ultrasound transducer that transmits and receives ultrasound waves to and from the subject. The fixation mechanism is provided in at least one of the capsule body unit and the sheath, to fixedly arrange the capsule body unit at a desired position in the sheath.

First Embodiment

The structure of an ultrasound diagnosis apparatus 1 according to a first embodiment will be described with reference to FIGS. 1 to 7. Further, a heart H is schematically illustrated in FIG. 1, and the like, to make it easier to understand that an observation object is the heart H.

Figure 1:
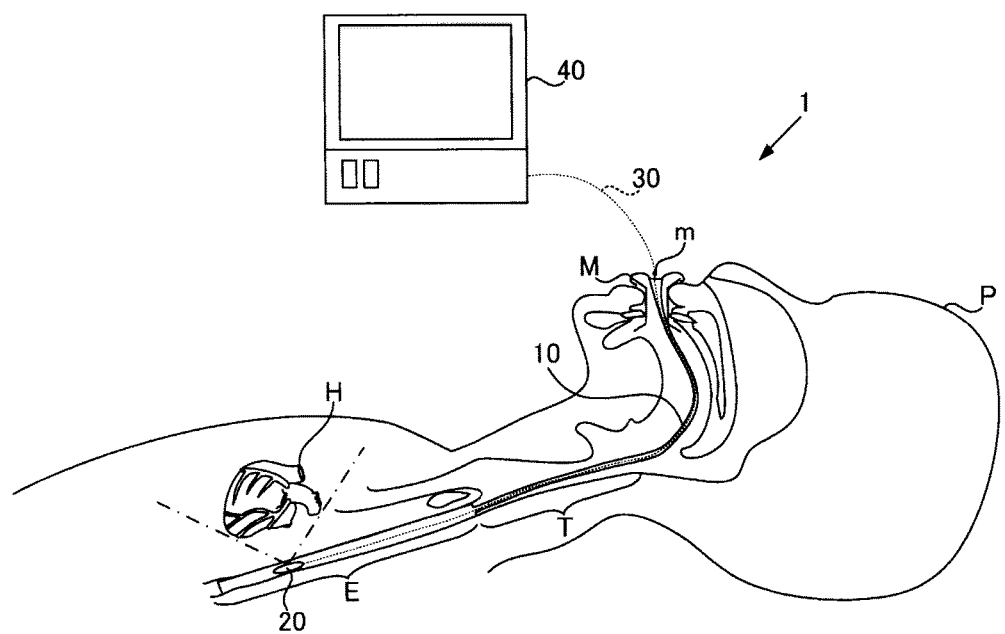
FIG. 1 is an overall view illustrating an ultrasound diagnosis apparatus according to a first embodiment.

FIG. 1 illustrates an example of observation of a desired organ (the heart H) in a subject P using the ultrasound diagnosis apparatus 1 according to the present embodiment. A sheath 10 is inserted into the inner cavity of the subject P. FIG. 1 illustrates an example in which the sheath 10 passes through a throat T to be inserted into the terminal end of an esophagus E (in the vicinity of the stomach cardia). A capsule body unit 20 transmits ultrasound waves to the heart H in a state that the unit 20 is fixedly arranged in the desired position (here, the esophagus E) in the sheath 10, and receives the reflected waves from the heart H as echo signals. Hereinafter, transmission of the ultrasound waves together with reception of the reflected waves is sometimes referred to as the "transmission and reception of ultrasound waves." The capsule body unit 20 transmits the echo signals to an external device 40 via a cable unit 30. The external device 40 processes the echo signals received from the capsule body unit 20, and generates and displays ultrasound images. Hereinafter, respective components will be described in detail.

<Sheath 10>

The sheath 10 is a hollow member having a specific length with an opening part formed at one end. The sheath 10 is made of a material capable of penetrating ultrasound waves (a material that neither reflects nor attenuates ultrasound waves). The sheath 10 is orally inserted into the inner cavity of a subject P by an operator, or the like. A liquid is injected inside the sheath 10 via the opening part located outside the subject P (details to be described later).

The specific length is decided by the observation object. For example, in the case of observing the heart H, it is necessary to arrange the capsule body unit 20 in the esophagus E. Therefore, the length of the sheath 10 is preferably predetermined by being estimated from the body type, age, and the like, of the subject P, since the sheath 10 needs to reach at least from the oral cavity of the subject P to the vicinity of the terminal end of the esophagus E (the cardiac of the stomach).

The sheath 10 according to the embodiments has a contracted shape (for example, a rounded flat shape to be described later) when a liquid is not filled inside. It becomes easy to insert a liquid into the inner cavity of the subject P by contracting the sheath 10.

Figure 2A:
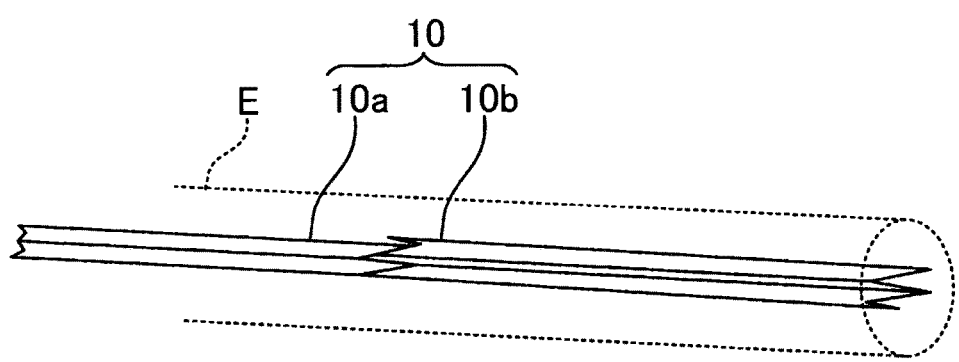
FIG. 2A is a view illustrating a sheath according to the first embodiment.
Figure 2B:
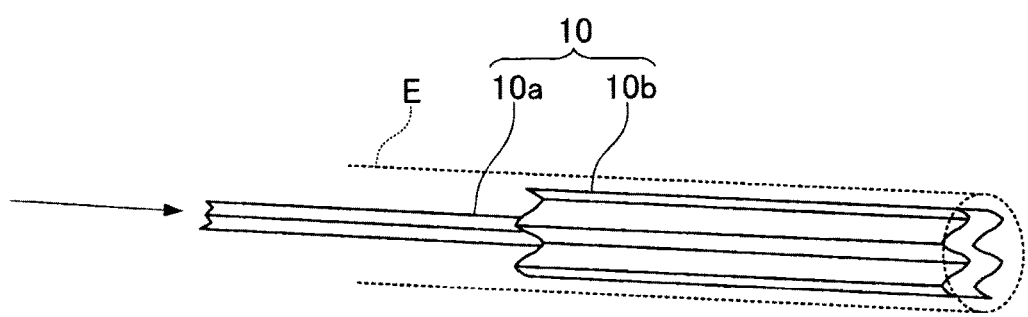
FIG. 2B is a view illustrating a sheath according to the first embodiment.
Figure 2C:
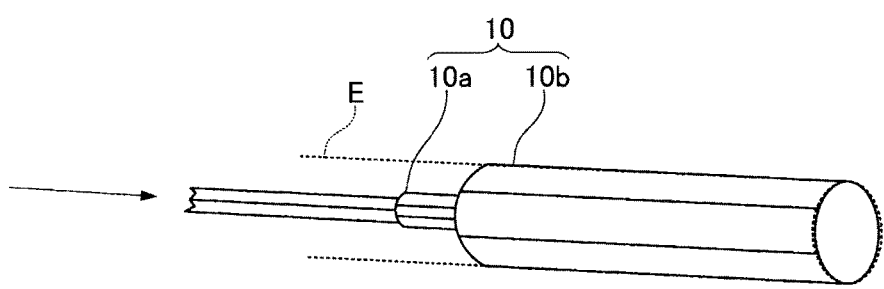
FIG. 2C is a view illustrating a sheath according to the first embodiment.

FIGS. 2A to 2C are perspective views schematically illustrating the sheath 10 inserted into the inner cavity of the subject P (the esophagus E). Arrows in FIGS. 2B and 2C indicate that the sheath 10 is filled with a liquid.

The sheath 10 according to the present embodiment includes a small diameter part 10a and a large diameter part 10b with a diameter larger than that of the small diameter part 10a. At least the outer peripheral surface of the large diameter part 10b needs to contact the inner wall surface of the inner cavity (the esophagus E) of the subject P. Accordingly, the diameter of the large diameter part 10b is preferably predetermined by being estimated from the body type, age, and the like, of the subject P. Further, the sheath 10 may have the entirely same diameter. In this case, the sheath 10 may be formed such that at least the portion on which the capsule body unit 20 is positioned only expands.

When no liquid is filled inside, the sheath 10 is formed into a rounded flat shape with the hollow part crushed (refer to FIG. 2A). In addition, the sheath 10 according to the present embodiment is configured such that the sheath easily becomes the rounded flat shape by folding the small diameter part 10a and the large diameter part 10b.

If a liquid (for example, water) capable of transmitting the ultrasound waves from the external device 40 (a liquid adjusting unit 48 to be described later) is injected into the sheath 10 while the sheath 10 is inserted into the esophagus E, the sheath 10 gradually expands (refer to FIG. 2B). Subsequently, when a liquid is filled inside, the outer peripheral surface of the large diameter part 10b of the sheath 10 contacts the inner wall surface of the inner cavity (the esophagus E) of the subject P (refer to FIG. 2C). The capsule body unit 20 is fixedly arranged in the large diameter part 10b of the sheath 10 in this state, enabling observation with the ultrasound waves.

Further, the inserted sheath 10 may potentially be transferred due to the peristalsis of the esophagus E, or the like. Therefore, it is possible to prevent the transfer of the sheath 10, for example, by fixing one end (the opening part side) of the sheath 10 to a mouthpiece M, and the like, arranged in the oral cavity of the subject P (refer to FIG. 1). In addition, a check valve, or the like, is preferably provided on a part of the sheath 10 such that the injected liquid does not flow outside the sheath 10.

In addition, not only a rounded flat shape but also any contracted shape for the sheath 10 may be provided as long as the sheath 10 can be easily inserted into the inner cavity of the subject P. For example, the flat shape is not necessarily rounded. Alternatively, the sheath 10 may be formed into an accordion structure capable of being longitudinally expandable.

<Capsule Body Unit 20>

The capsule body unit 20 according to the present embodiment will be described with reference to FIGS. 3A to 6D.

Figure 3A:
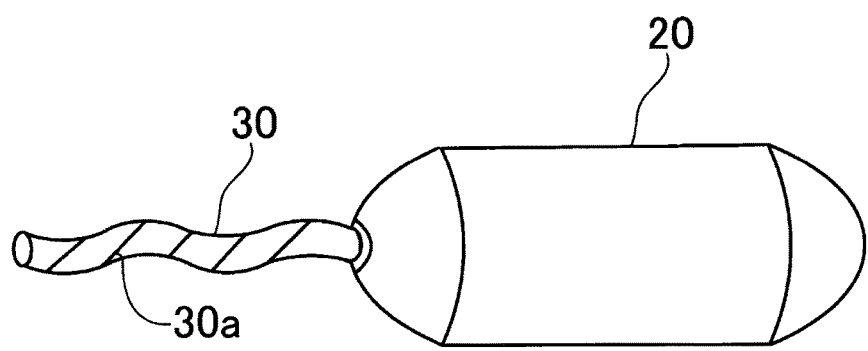
FIG. 3A is a view illustrating a capsule body unit according to the first embodiment.
Figure 3B:
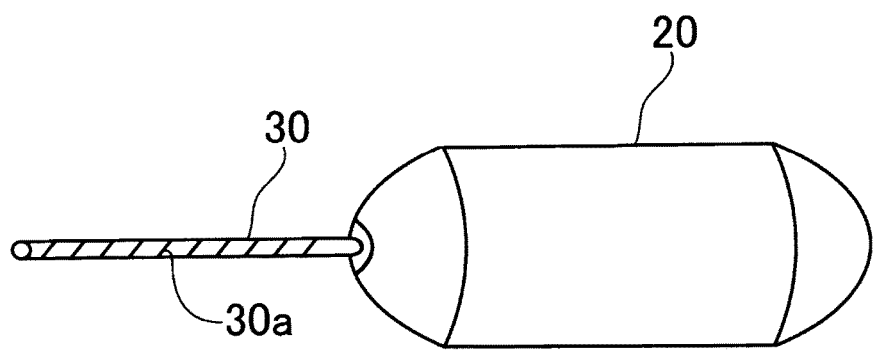
FIG. 3B is a view illustrating a capsule body unit according to the first embodiment.
Figure 3C:
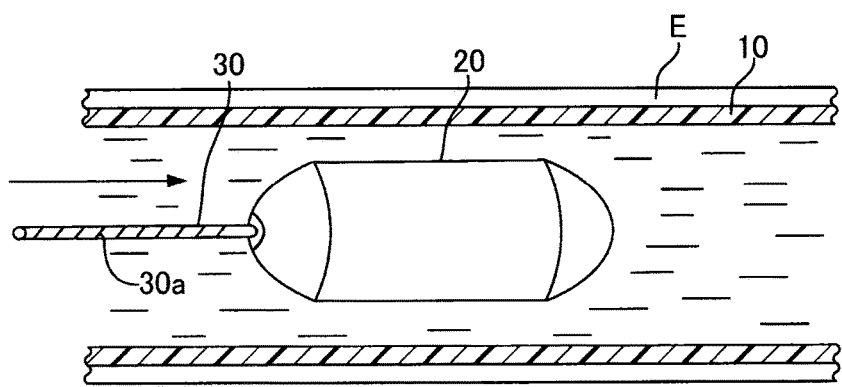
FIG. 3C is a view illustrating a capsule body unit according to the first embodiment.

At first, the outline, and the like, of the capsule body unit 20 will be described with reference to FIGS. 3A to 3C. FIGS. 3A and 3B are pattern views illustrating the capsule body unit 20. FIG. 3C is a pattern view illustrating the capsule body unit 20 inserted into the sheath 10. Further, only a part of the cable unit 30 is illustrated in FIGS. 3A to 3C.

The capsule body unit 20 is formed in a capsule shape capable of easily penetrating the throat of the subject P. The external peripheral part of the capsule body unit 20 is made of a material capable of penetrating ultrasound waves (a material that neither reflects nor attenuates ultrasound wave). The structure for transmitting and receiving ultrasound, and the like (described later), are stored inside the capsule body unit 20.

According to the present embodiment, one end of the cable unit 30 is coupled to the rear end of the capsule body unit 20. The other end of the cable unit 30 is coupled to the external device 40. A signal line, and the like, for transmitting and receiving signals between the capsule body unit 20 and the external device 40 are arranged inside the cable unit 30.

In addition, the cable unit 30 has flexibility (a so-called "strap-shape," refer to FIG. 3A). Therefore, the cable unit 30 is arranged along the shape inside the sheath 10 with the capsule body unit 20 indwelling in the sheath 10 inserted into the inner cavity (the esophagus E) of the subject P (refer to FIG. 1).

On the other hand, the cable unit 30 of the present embodiment is configured such that the flexibility thereof is lowered when contorted. According to a specific example, as illustrated in FIG. 3A, a groove 30a is formed on the outer peripheral surface of the cable unit 30. When the cable unit 30 is contorted, the flexibility of the cable unit 30 is lowered by being twisted along the groove 30a (the cable unit 30 is formed into a so-called "paper-twisted shape;" refer to FIG. 3B). The capsule body unit 20 can be inserted into the sheath 10 filled with a liquid by inserting the cable unit 30 thus formed into the paper-twisted shape into the sheath 10 (refer to FIG. 3C; the arrow indicates the insertion direction of the capsule body unit 20). Further, by pulling the cable unit 30, it is possible to transfer the capsule body unit 20 in the opposite direction of the insertion direction. The capsule body unit 20 may be transferred in the opposite direction by contorting the cable unit 30 in the opposite direction of the twisting direction, with flexibility provided cable unit 30.

In addition, a strap for transferring the capsule body unit 20 may be provided other than the cable unit 30, leaving the cable unit 30 flexible. One end of the strap is coupled to the rear end of the capsule body unit 20. The strap is configured such that the flexibility is lowered if the strap is contorted. As a specific example, a groove is formed on the strap. When the strap is contorted, the flexibility of the strap is lowered by being twisted along the groove. Thus, the capsule body unit 20 can be inserted into the sheath 10 filled with a liquid by inserting the strap in the paper-twisted shape into the sheath 10. Further, by pulling the strap, it is possible to transfer the capsule body unit 20 in the opposite direction of the insertion direction. The capsule body unit 20 may be transferred in the opposite direction by contorting the strap in the opposite direction of the twisting direction, with the flexibility provided to the strap.

Thus, the capsule body unit 20 can be transferred in the sheath 10 by pushing and pulling the cable unit 30 (or the strap provided other than the cable unit) through the operator. The capsule body unit 20 does not come into contact with the inner wall of the inner cavity of the subject P as the capsule body unit 20 is transferred in the inner cavity of the subject P via the sheath 10. Consequently, it becomes possible to prevent the inner wall from being damaged due to the transfer of the capsule body unit 20.

Further, the method of inserting the capsule body unit 20 into the sheath 10 and the method of transferring the capsule body unit 20 within the sheath 10 are not limited to the abovementioned examples.

For example, the capsule body unit 20 may be arranged at one end of the sheath 10 (opening part) in advance. When a liquid is injected from the external device 40 into the sheath 10 in this state, it becomes possible to push the capsule body unit 20 into the large diameter part 10b of the sheath 10 due to pressure generated from the injection of the liquid. Subsequently, the position of the capsule body unit 20 can be adjusted by pushing and pulling the cable unit 30.

Alternatively, a self-propelled mechanism (for example, a mechanism that advances and retreats within the liquid filled in the sheath 10 by rotating a screw provided at the rear end of the capsule body unit 20) can be provided to the capsule body unit 20. The operator does not need to push and pull the cable unit 30 by providing the self-propelled mechanism. As a result, the capsule body unit 20 can be more conveniently inserted, transferred, and the like, in the sheath 10.

In addition, when the observation is terminated, the capsule body unit 20 can be removed from the inside of the sheath 10 by pulling the cable unit 30. Alternatively, the external device 40 (the liquid adjusting unit 48, to be described later) can be used to evacuate the liquid in the sheath 10 with the capsule body unit 20 arranged. Therefore, when the observation is terminated, the sheath 10 is contracted by evacuating the liquid in the sheath 10 with the external device 40. By removing the opening part side (the part on the outside of the subject P) of the contracted sheath 10 from the subject P, the operator can remove the capsule body unit 20 located inside thereof together. In this case, as the cable unit 30 does not need to be directly operated, it is possible to prevent the breaking of signal lines, or the like, arranged inside the cable unit 30.

In addition, the cable unit 30 may be provided with a marker m (or a scale) (refer to FIG. 1). The operator can visualize how much of the cable unit 30 (the capsule body unit 20) is inserted into the inner cavity of the subject P (the position of the capsule body unit 20 in the inner cavity of the subject P) by the marker m. For example, when the operator desires to observe the heart H by indwelling the capsule body unit 20 in the esophagus E, the marker m is provided in the cable unit 30 based on the general length from the oral cavity to the esophagus E. In other words, the marker m is provided such that the length of the cable unit 30 between the marker m and the capsule body unit 20 becomes approximately identical with the general length from the oral cavity to the esophagus E. The operator confirms the position of the marker m while inserting the capsule body unit 20 into the sheath 10 by pushing the cable unit 30 into the sheath 10. When the marker m reaches the vicinity of the oral cavity, the operator can recognize that the capsule body unit 20 is positioned in the esophagus E.

Hereinafter, with reference to FIGS. 4 to 6D, the inner structure of the capsule body unit 20 will be described.

Figure 4:
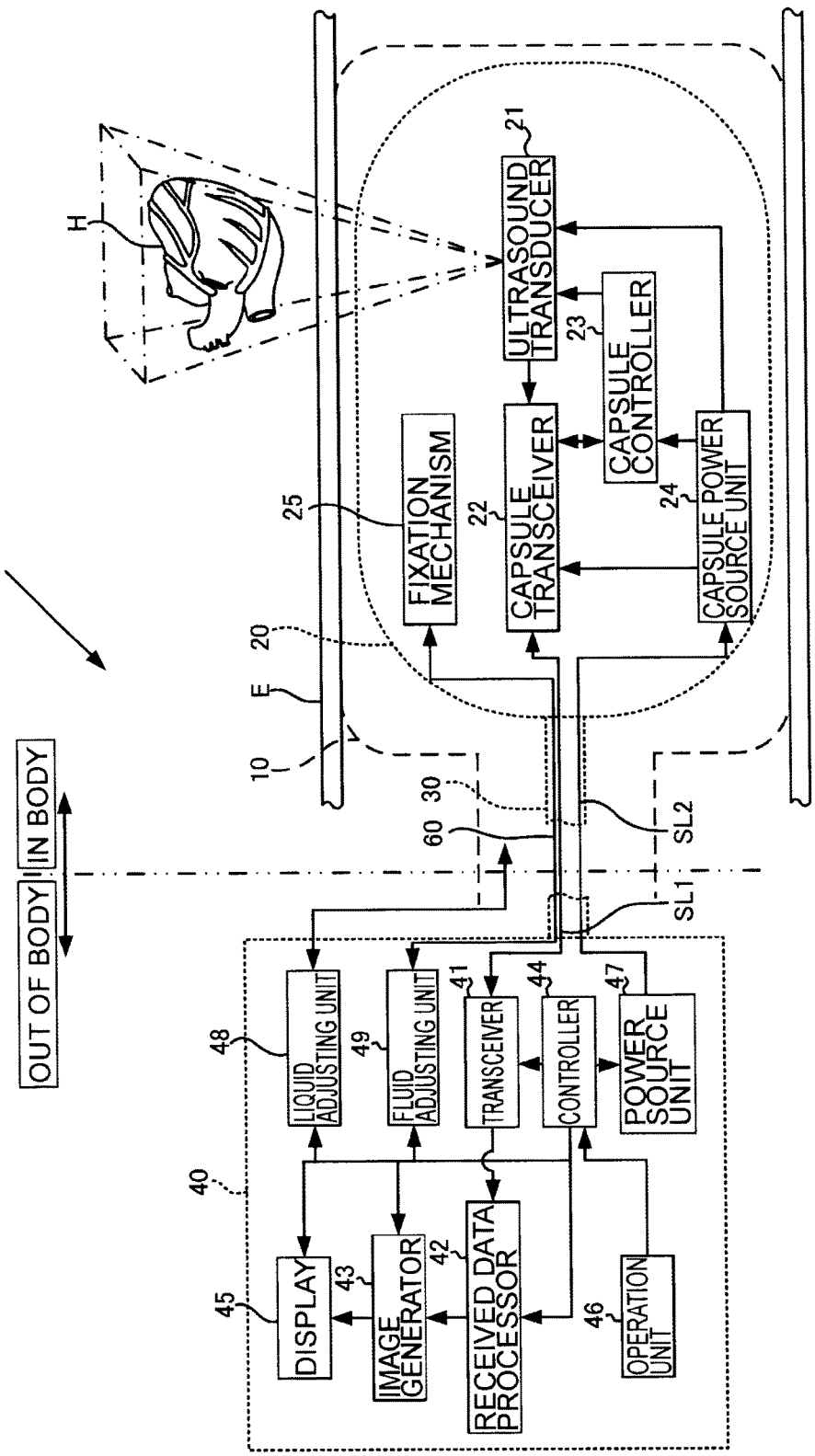
FIG. 4 is a block diagram illustrating the outline of the ultrasound diagnosis apparatus according to the first embodiment.

FIG. 4 is a block diagram illustrating the structures of the capsule body unit 20 and the external device 40. The capsule body unit 20 includes an ultrasound transducer 21, a capsule transceiver 22, a capsule controller 23, a capsule power source unit 24, and a fixation mechanism 25.

The ultrasound transducer 21 is stored in the capsule body unit 20. Based on driving signals from the capsule controller 23, the ultrasound transducer 21 transmits ultrasound waves from an emission surface. In addition, the ultrasound transducer 21 receives the reflected waves from the subject P, and transfers the echo signals to the capsule transceiver 22.

Piezoelectric bodies and MUT (Micromachining Ultrasound Transducer) elements can be used as transducer elements to configure the ultrasound transducer 21. MUT elements include cMUT (Capacitive Micromachining Ultrasound Transducer: capacitance transducer) and pMUT (Piezoelectric Micromachining Ultrasound Transducer: piezoelectric transducer).

In the present embodiment, an example is described in which a 2D array for transmitting and receiving ultrasound waves by electronically scanning a plurality of transducer elements arranged in the 2D array is utilized as the ultrasound transducer 21. Ultrasound waves can be transmitted and received in a square pyramid-shaped three-dimensional domain by the 2D array (refer to FIG. 4).

The capsule transceiver 22 transmits control signals from the external device 40 (a controller 44, to be described later) to the capsule controller 23. Based on these control signals, the capsule controller 23 transmits driving signals to the ultrasound transducer 21. Subsequently, the capsule transceiver 22 receives echo signals based on the reflected waves received by the ultrasound transducer 21. The capsule transceiver 22 outputs the echo signals to the external device 40 (a transceiver 41, to be described later). According to the present embodiment, the control signals, and the like, are transmitted and received between the capsule body unit 20 and the external device 40 via a signal line SL1 arranged in the cable unit 30.

As a specific example, the capsule controller 23 supplies driving signals to the ultrasound transducer 21 to two-dimensionally scan the ultrasound transducer 21, causing the heart H to transmit ultrasound waves. The capsule controller 23, for example, includes a clock generator, a transmission delay circuit, and a pulsar circuit (not illustrated). The clock generator serves to generate clock signals that decide the transmission timing and transmission frequencies of ultrasound signals. The transmission delay circuit carries out transmission focus by delaying the transmission time of ultrasound waves according to the delay time for convergence in order to converge ultrasound waves on the observation object and the delay time for the beam steering to the observation object. The pulsar circuit has pulsars, the number of which is equivalent to the number of individual channels corresponding to the transmitting elements. The pulsar circuit generates a driving pulse (driving signal) at delayed transmission timing, and supplies the driving pulse (driving signal) to the transmitting element that forms the ultrasound transducer 21.

In addition, by causing the received echo signals to be subjected to delaying process, the capsule transceiver 22 converts the analog echo signals into digital data (received data) provided with phasing and addition. The capsule transceiver 22 includes, for example, a gain circuit, an A/D converter, a reception delay circuit, and an adder (not illustrated). The gain circuit amplifies (gains) echo signals output from the receiving elements of the ultrasound transducer 21 for each reception channel. The A/D converter converts the amplified echo signals into digital signals. The reception delay circuit provides the delay time necessary for deciding the reception directivity of the echo signals converted into the digital signals. Specifically, the reception delay circuit provides the delay time for focusing and the delay time for beam steering to the digital echo signals. The adder adds the delayed echo signals. According to this addition, reflected signals from the target are emphasized. In other words, according to the reception delay circuit and the adder, the echo signals acquired from the observation object are phased and added. The capsule transceiver 22 outputs the beamformed echo signals (received data) to the external device 40.

The capsule power source unit 24 gets the electric power from the external device 40 (a power source unit 47, to be described later). The capsule power source unit 24 distributes the supplied electricity to the ultrasound transducer 21, the capsule transceiver 22, and the capsule controller 23. According to the present embodiment, electricity from the external device 40 is supplied via a signal line SL2 arranged in the cable unit 30.

The fixation mechanism 25 disposed in the capsule body unit 20 serves to fixedly arrange the capsule body unit 20 at the desired position in the large diameter part 10b of the sheath 10. It is possible to indwell the capsule body unit 20 in the inner cavity (the esophagus E) of the subject P by fixedly arranging the capsule body unit 20 at the desired position.

The desired position is the position at which the capsule body unit 20 can transmit and receive ultrasound waves to and from the observation object. Whether or not the capsule body unit 20 is placed at the desired position is determined, for example, by observing ultrasound images acquired through transmission and reception of ultrasound waves via the operator.

Figure 5A:
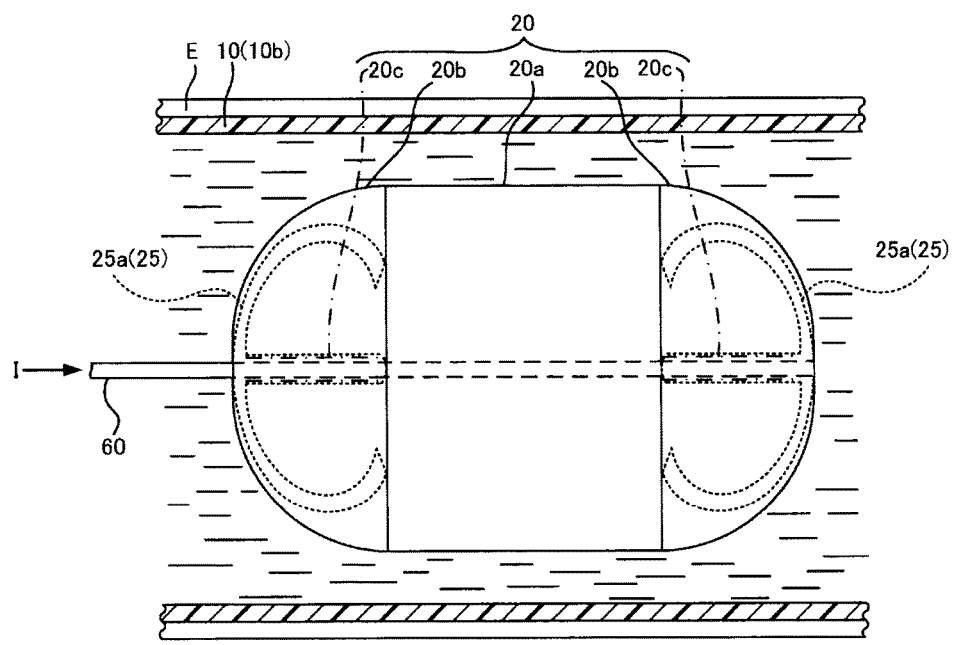
FIG. 5A is a view illustrating an example of a fixation mechanism according to the first embodiment.
Figure 5B:
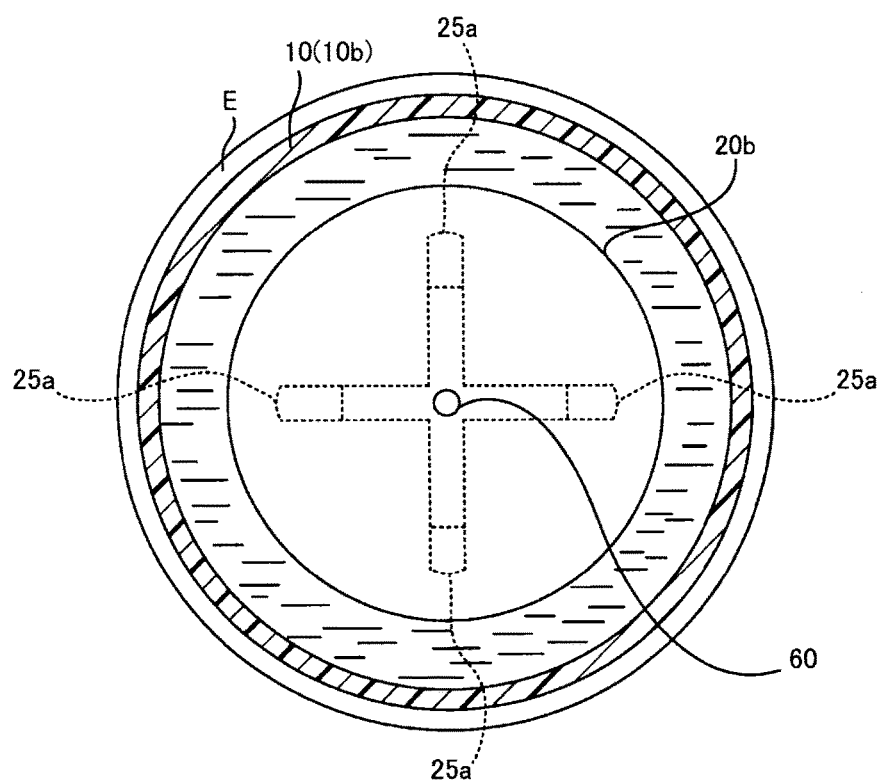
FIG. 5B is a view illustrating an example of a fixation mechanism according to the first embodiment.
Figure 5C:
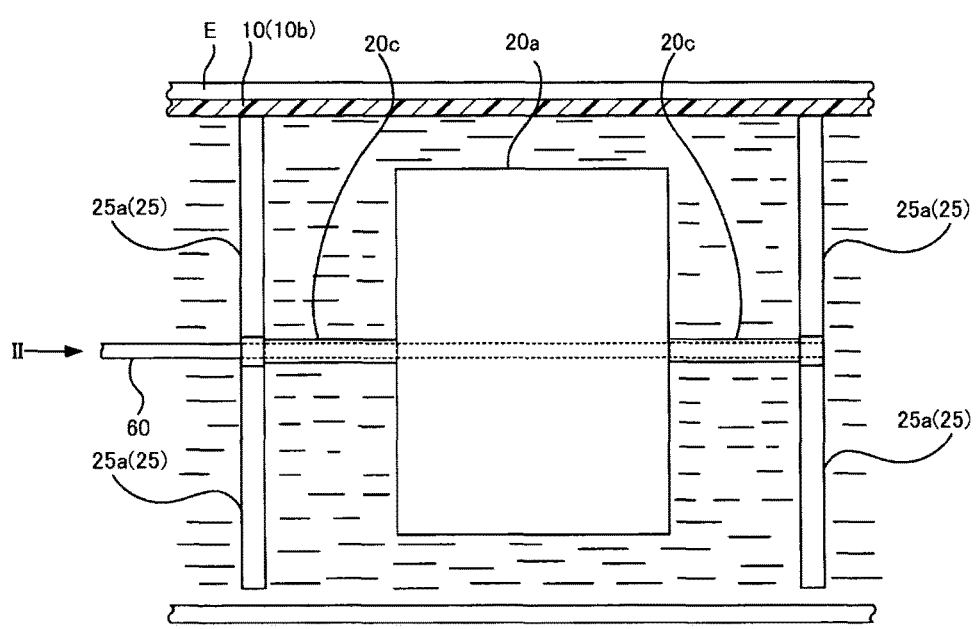
FIG. 5C is a view illustrating an example of a fixation mechanism according to the first embodiment.
Figure 5D:
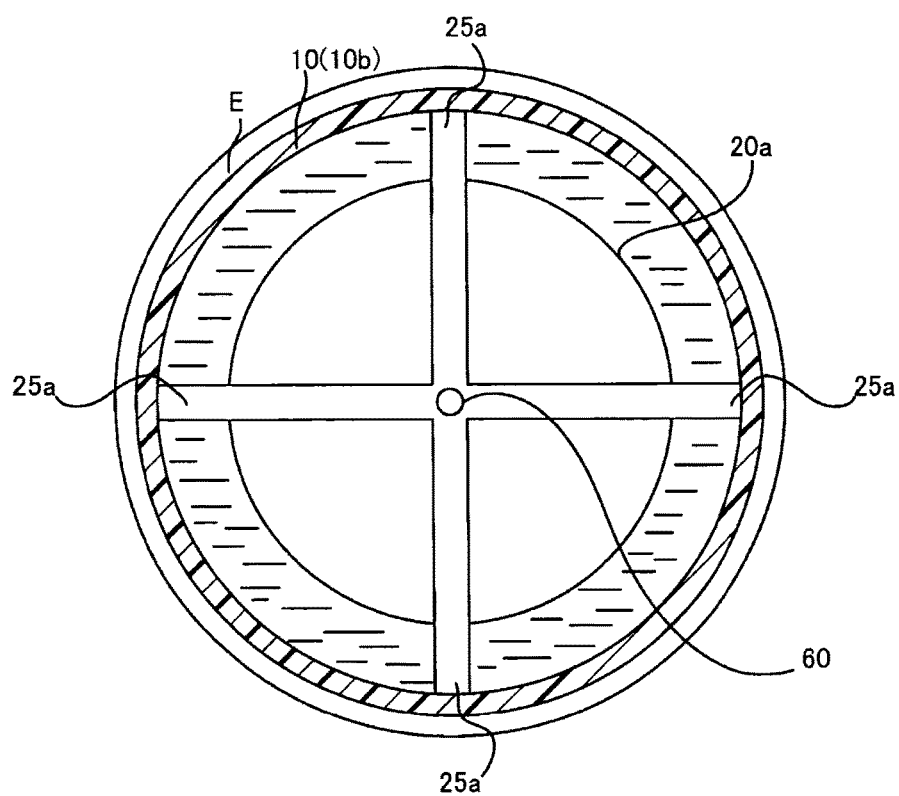
FIG. 5D is a view illustrating an example of a fixation mechanism according to the first embodiment.

Hereinafter, with reference to FIGS. 5A to 5D, the detailed structure of the fixation mechanism 25 according to the present embodiment will be described. FIGS. 5A and 5C are side views of the capsule body unit 20 inserted into the large diameter part 10b of the sheath 10. FIG. 5B is a front view of the capsule body unit 20 in FIG. 5A as seen from a direction I. FIG. 5D is a front view of the capsule body unit 20 in FIG. 5C as seen from a direction II. Further, in FIGS. 5A to 5D, the illustrations of respective components stored in the capsule body unit 20 other than the fixation mechanism 25 and the cable unit 30 are omitted.

The capsule body unit 20 illustrated in FIGS. 5A to 5D includes a main body part 20a, a hemisphere part 20b, and an axial part 20c. The ultrasound transducer 21, and the like, and their respective components stored in the capsule body unit 20 (other than the fixation mechanism 25) are arranged in the main body part 20a. The hemisphere part 20b is a hollow member arranged such that the hemisphere part 20b is attachable to and detachable from the main body part 20a. The fixation mechanism 25 is arranged inside the hemisphere part 20b. The axial part 20c is a member protruding from the main body part 20a to the inside of the hemisphere part 20b and, further, is a member coupling the main body part 20a with the fixation mechanism 25.

The fixation mechanism 25 according to the present embodiment includes an expansion unit 25a.

The expansion unit 25a disposed in the capsule body unit 20 expands by being supplied with a fluid from the outside. The expansion unit 25a is configured by a member with elasticity such as a resin material, and the like.

As a fluid injected into the expansion unit 25a, for example, any of a liquid such as water, or the like, or a gas such as air, or the like, is available. However, gas attenuates ultrasound waves. Therefore, in the case of using a gas as a fluid, the fixation mechanism 25 (the expansion unit 25a) is preferably provided such that it is positioned outside the transmission and reception directions of ultrasound waves by the ultrasound transducer 21 with the capsule body unit 20 fixedly arranged therein (expanded state). In this case, the fixation mechanism 25 never prevents transmission and reception of ultrasound waves due to the ultrasound transducer 21.

According to the present embodiment, a plurality of the expansion units 25a is arranged at the front and rear ends of the capsule body unit 20. For example, as illustrated in FIGS. 5A and 5B, four expansion units 25a of the present embodiment are provided at the front and rear ends of the capsule body unit 20, respectively. In addition, each of the expansion units 25 is arranged in the hemisphere part 20b in a curved state. The expansion part 25a and the main body part 20a are coupled with each other by the axial part 20c.

In addition, each of the plurality of the expansion units 25a is communicated with a fluid passage 60. The fluid passage 60 provided in the cable unit 30 is a passage communicated with the external device 40 (a fluid adjusting unit 49, to be described later). According to the present embodiment, the fluid passage 60 penetrates the main body part 20a to be communicated with each of the expansion units 25a arranged at the front end of the capsule body unit 20. In the hemisphere part 20b, the fluid passage 60 is inserted into the axial part 20c.

If a fluid is supplied to each of the expansion units 25a via the fluid passage 60 from the external device 40, the expansion unit 25a expands. The hemisphere part 20b is detached with the expansion of the expansion unit 25a, after which, the expansion unit 25a protrudes outside the capsule body unit 20. The front end part of each of protruded expansion units 25a is brought into contact with the inner wall of the large diameter part 10b of the sheath 10 (refer to FIGS. 5C and 5D). According to the present embodiment, the four expansion units 25a broaden in the cross-shape by being expanded, while each front end part is brought into contact with the inner wall of the large diameter part 10b of the sheath 10 (refer to FIG. 5D).

Thus, by expanding the expansion unit 25a such that it is brought into contact with the inner wall of the large diameter part 10b of the sheath 10, it becomes possible to fixedly arrange the capsule body unit 20 (the main body part 20a) at the desired position in the large diameter part 10b of the sheath 10. In FIGS. 5C and 5D, illustrations of the detached hemisphere parts 20b are omitted. In addition, it is also possible to provide a porous part capable of protruding outside of the capsule body unit 20 in the hemisphere part 20b when the expansion unit 25a expands. In this case, the structure in which the hemisphere part 20b is detached becomes unnecessary.

Generally, as the esophagus E has elasticity and peristalsis, it is difficult to indwell a medical apparatus, and the like, therein. However, it is possible to indwell the capsule body unit 20 in the subject P by fixedly arranging the capsule body unit 20 to the large diameter part 10b of the sheath 10. Subsequently, it becomes possible to observe the observation object of the heart H, or the like, with ultrasound waves by the indwelled capsule body unit 20. When the observation ends, the expansion unit 25a is contracted to return to the original state (the states of FIGS. 5A and 5B) by evacuating the fluid in the expansion unit 25a with the external device 40 (the fluid adjusting unit 49, to be described later).

Further, the structure of the fixation mechanism 25 according to the present embodiment is not limited to the above if the structure can fixedly arrange the capsule body unit 20 when the expansion unit 25a comes into direct contact with the inner wall of the large diameter part 10b of the sheath 10.

Figure 6A:
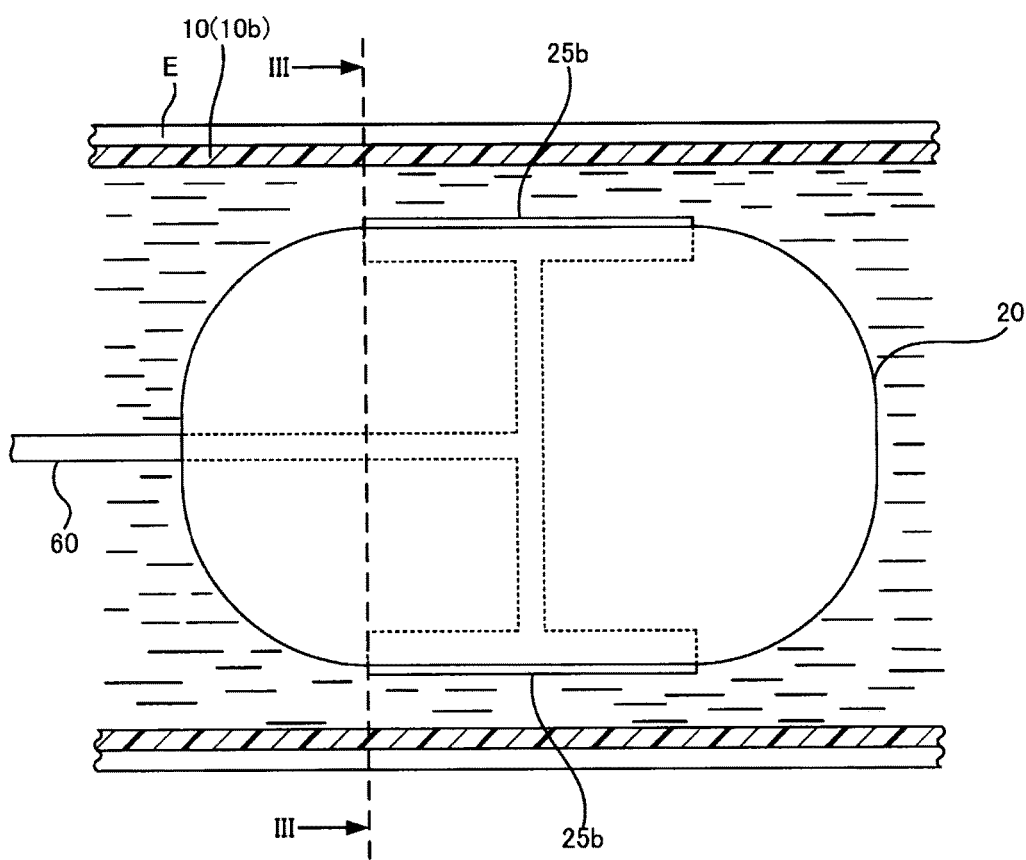
FIG. 6A is a view illustrating another example of the fixation mechanism according to the first embodiment.
Figure 6B:
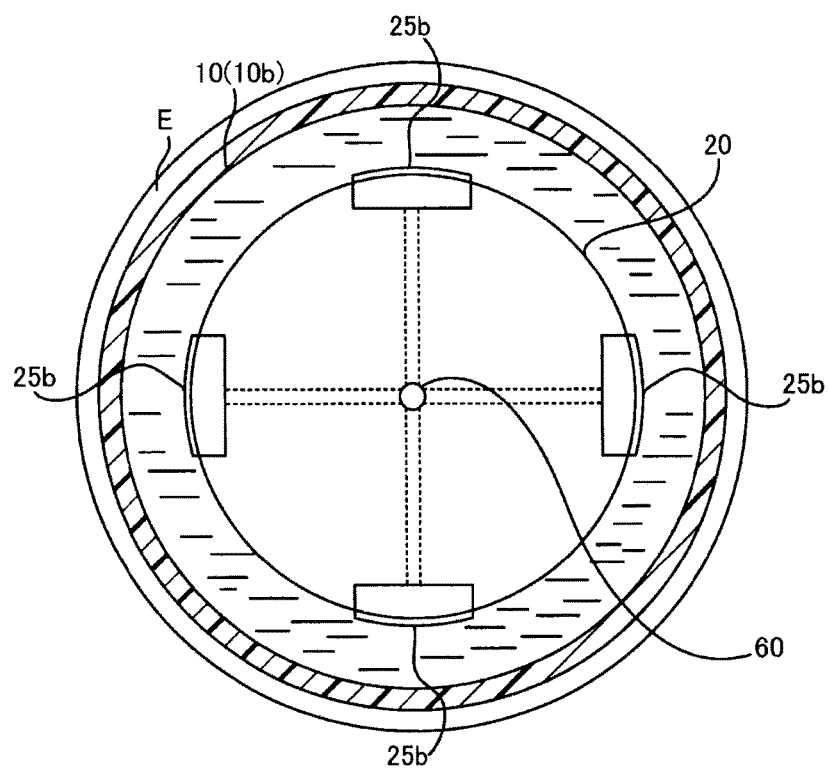
FIG. 6B is a view illustrating another example of the fixation mechanism according to the first embodiment.
Figure 6C:
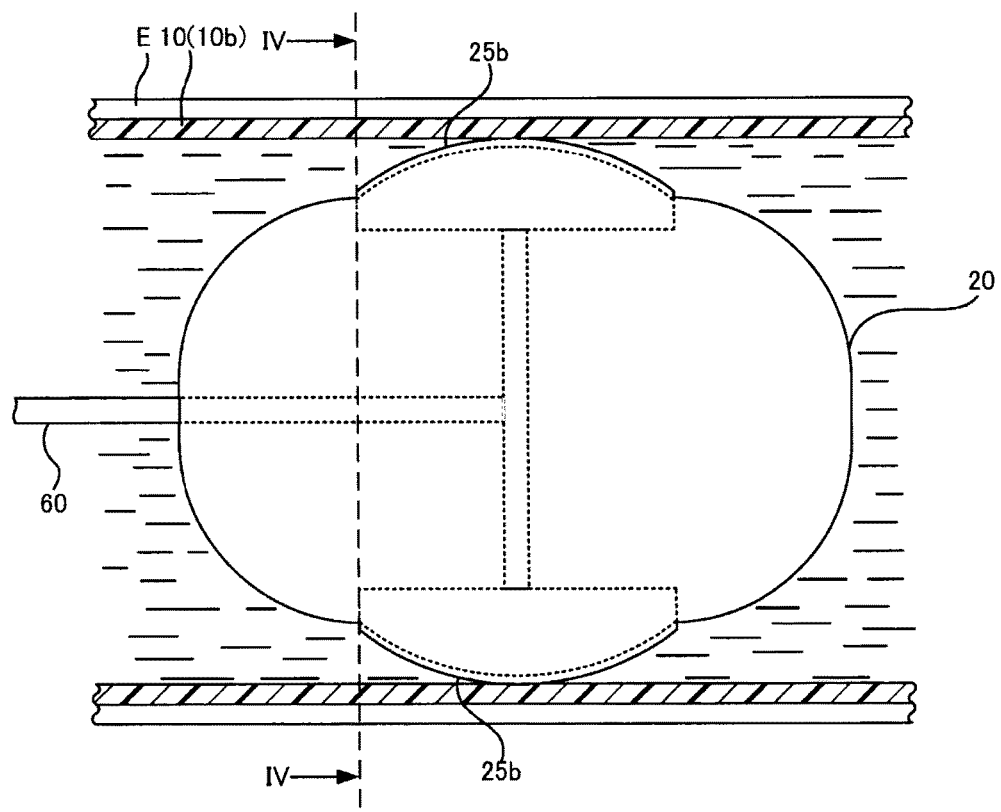
FIG. 6C is a view illustrating another example of the fixation mechanism according to the first embodiment.
Figure 6D:
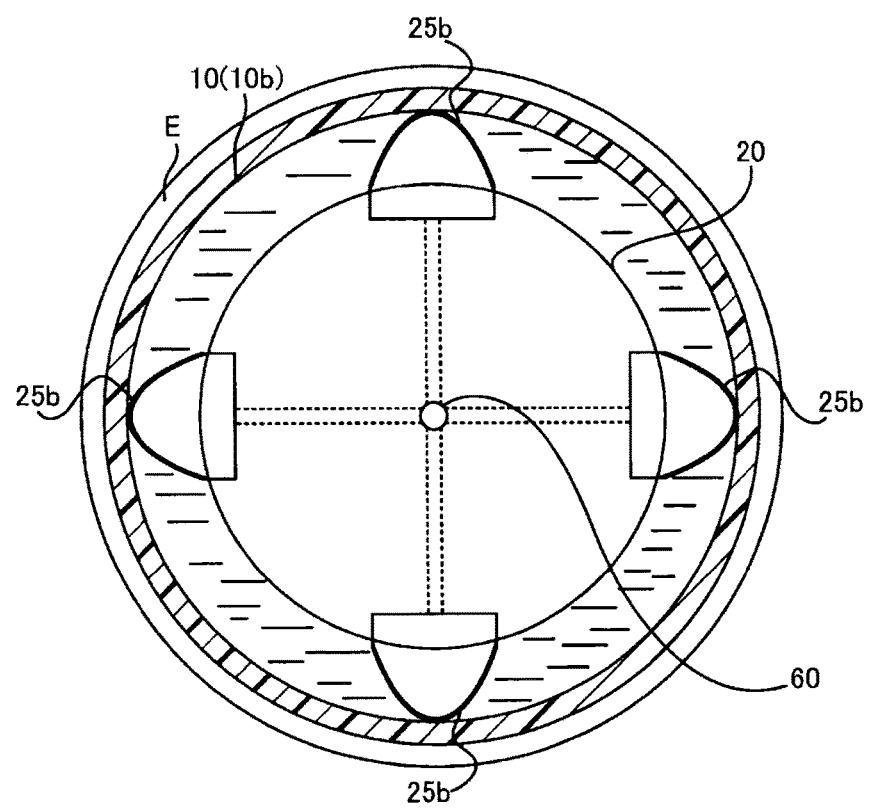
FIG. 6D is a view illustrating another example of the fixation mechanism according to the first embodiment.

Another example of the fixation mechanism 25 according to the present embodiment will be described with reference to FIGS. 6A to 6D. FIGS. 6A and 6C are side views of the capsule body unit 20 inserted into the large diameter part 10b of the sheath 10. FIG. 6B is a sectional view taken along a direction III-III in FIG. 6A. FIG. 6D is a sectional view taken along a direction IV-IV in FIG. 6C. In FIGS. 6A to 6D, illustrations of respective components stored in the capsule body unit 20 other than the fixation mechanism 25 and the cable unit 30 are omitted.

According to this example, a balloon member 25b is provided on the outer peripheral surface of the capsule body unit 20. Four balloon members 25b are provided at the radially-opposed positions of the capsule body unit 20 (refer to FIGS. 6B and 6D; in FIGS. 6A and 6C, illustrations of two balloon members among the four balloon members 25b are omitted). The balloon member 25b is formed by a member with elasticity such as a resin material, and the like.

If a fluid is supplied from the external device 40 to the balloon member 25b via the fluid passage 60, the balloon member 25b expands. The expanded balloon member 25b comes into contact with the inner wall of the large diameter part 10b of the sheath 10 (refer to FIGS. 6C and 6D). As a result, the balloon member 25b can fixedly arrange the capsule body unit 20 at the desired position in the large diameter part 10b of the sheath 10. The balloon member 25b of the present embodiment is an example of "an expansion unit."

It is sufficient for the expansion unit to be capable of fixedly arranging the capsule body unit 20 at the desired position in the large diameter part 10b of the sheath 10. In other words, the number, shape, position, and the like, of the expansion unit are not limited to the above examples.

According to the present embodiment, the sheath 10, the capsule body unit 20, and the fixation mechanism 25 relate to an example of "the ultrasound medical apparatus."

<External Device 40>

Hereinafter, with reference to FIG. 4, the structure of the external device 40 according to the present embodiment will be described.

The external device 40 includes the transceiver 41, a received data processor 42, an image generator 43, the controller 44, a display 45, an operation unit 46, the power source unit 47, the liquid adjusting unit 48, and the fluid adjusting unit 49.

The transceiver 41 receives the echo signals from the capsule transceiver 22, and outputs the echo signals to the received data processor 42. In addition, the transceiver 41 transmits the control signals from the controller 44 to the capsule transceiver 22.

The received data processor 42 carries out various signal processing on the echo signals output from the transceiver 41. For example, the received data processor 42 includes a B mode processor. The B mode processor receives echo signals from the transceiver 41 to extract the amplitude information of the echo signals. In addition, the received data processor 42 may have a CFM (Color Flow Mapping) processor. The CFM processor gets the blood-flow information. In addition, the received data processor 42 may have a Doppler processor. The Doppler processor extracts Doppler shift frequency components by phase-detecting the echo signals, and generates Doppler frequency distribution representing the blood-flow velocity by carrying out the FFT processing. Received data processor 42 outputs echo signals provided with the signal processing to the image generator 43.

The image generator 43 processes the echo signals output from the received data processor 42 after being signal-processed, and generates image data (ultrasound image data).

The controller 44 controls the operations of respective components of the ultrasound diagnosis apparatus 1. For example, the controller 44 transmits driving signals for driving the ultrasound transducer 21 to the capsule transceiver 22 via the transceiver 41, and controls the transmission and reception of ultrasound waves. Alternatively, the controller 44 causes the display 45 to display images (ultrasound images) based on the image data (ultrasound image data) generated by the image generator 43.

The display 45 is formed by a monitor such as a CRT, a liquid crystal display, or the like. The operation unit 46 is formed by an input device such as a keyboard, a mouse, and the like. The operator carries out the transmission and reception, and the like, of ultrasound waves by the capsule body unit 20 via the operation unit 46.

The liquid adjusting part 48 is a device for injecting a liquid into the sheath 10 or evacuating the liquid filled in the sheath 10. The liquid may be stored in the liquid adjusting unit 48 itself or may be supplied from outside (for example, a water tap).

The fluid adjusting unit 49 is a device for supplying a fluid or evacuating the supplied fluid, in order for the fixation mechanism 25 (the expansion unit 25a, and the like) to function. The fluid may be stored in the fluid adjusting unit 49 itself or may be supplied from outside (for example, a water tap).

The liquid adjusting unit 48 and the fluid adjusting unit 49 can be controlled via either automatic control by the controller 44 or manual control by the operator.

Further, it is not necessary to install all of the respective components of the external device 40 in one device as illustrated in FIG. 1. For example, the external device 40 carries out the procedures for the generation of image data by the image generator 43. The controller 44 transmits the generated image data to a display located at a remote place (for example, a large hospital where a specialist works) through a communication line. Subsequently, by observing the images based on the present image data displayed on the display with a specialist, it becomes possible to instruct the operator in a location away therefrom to carry out an appropriate processing on the subject. In addition, in this case, the size of the ultrasound diagnosis apparatus 1 itself can be downsized since the external device 40 does not need to be provided with the display 45. Alternatively, it is also possible to provide a dedicated tank as the liquid adjusting unit 48 and the fluid adjusting unit 49.

The sheath 10, the capsule body unit 20, the fixation mechanism 25, the image generator 43, and the controller 44 according to the present embodiment relate to an example of "the ultrasound diagnosis apparatus."

<Operation>

The operation of the ultrasound diagnosis apparatus 1 according to the present embodiment will be described with reference to FIG. 7. Here, an example of observing the heart H by indwelling the capsule body unit 20 in the esophagus E will be described.

At first, the operator inserts the sheath 10 into the inner cavity of the subject P (S10). The inserted sheath 10 is fixed to the mouthpiece M in order to prevent the esophagus E from being transferred by peristalsis, or the like.

The controller 44 causes the liquid adjusting unit 48 to inject a liquid into the sheath 10 (S11). The sheath 10, into which the liquid is injected, expands, while the outer peripheral surface of the large diameter part 10b contacts the inner wall surface of the esophagus E.

The operator places the capsule body unit 20 into the sheath 10, and inserts the capsule body unit 20 into a desired position by pushing the cable unit 30 (S12).

The controller 44 causes the fluid adjusting unit 49 to inject a fluid in the expansion unit 25a (S13).

The expansion unit 25a injected with fluid expands to come into contact with the inner wall of the large diameter part 10b of the sheath 10, thereby fixedly arranging the capsule body unit 20 at the desired position in the large diameter part 10b of the sheath 10 (S14).

Subsequently, the observation of ultrasound waves is carried out by the capsule body unit 20 (S15).

Once the observation ends, the operator removes the sheath 10 and the capsule body unit 20 from the subject P (S16). Specifically, at first, the controller 44 causes the fluid adjusting unit 49 to evacuate the fluid in the expansion unit 25a. Due to evacuation of the fluid, the expansion unit 25a is contracted. In other words, the fixed arrangement of the capsule body unit 20 is released. Consequently, it becomes possible to transfer the capsule body unit 20 in the sheath 10. Next, the controller 44 causes the liquid adjusting unit 48 to evacuate the liquid in the sheath 10. Due to evacuation of the liquid, the sheath 10 is contracted. In other words, the state in which the outer peripheral surface of the large diameter part 10b of the sheath 10 contacts the inner wall surface of the esophagus E is dissolved. As a result, it becomes possible to transfer the sheath 10 within the inner cavity of the subject P. It is possible to simultaneously remove the sheath 10 and the capsule body unit 20 from the subject P by pulling the opening part side of the sheath 10 together with the cable unit 30 with the capsule body unit 20 arranged in the sheath 10. Further, in the case of removing only the capsule body unit 20, the operator may pull the cable unit 30 alone.

The present embodiment is described by taking the heart H, for example, as the observation object; however, the observation object is not limited to this. The structure of the present embodiment can be applied to any site if the site can be observed by ultrasound waves.

<Operation and Effect>

The operation and the effect of the present embodiment will be described.

The ultrasound medical apparatus according to the present embodiment includes the sheath 10, the capsule body unit 20, and the fixation mechanism 25. The sheath 10 is inserted into the inner cavity of the subject P, and the outer peripheral surface (the outer peripheral surface of the large diameter part 10b) contacts the inner wall surface of the inner cavity of the subject P with a liquid filled inside. The capsule body unit 20 is inserted inside the sheath 10 (the inside of the large diameter part 10b), and stores the ultrasound transducer 21 that transmits and receives ultrasound waves to and from the subject P (the observation object in the subject P). The fixation mechanism 25 is provided in the capsule body unit 20, and fixedly arranges the capsule body unit 20 at a desired position in the sheath 10 (in the large diameter part 10b).

Thereby, the fixation mechanism 25, which fixedly arranges the capsule body unit 20 at the desired position in the sheath 10, is provided. Therefore, according to the ultrasound medical apparatus of the present embodiment, it becomes possible to indwell the capsule body unit 20 capable of transmitting and receiving ultrasound waves in the observation object in the subject P. It becomes possible to continuously observe the observation object (for example, the heart H) with ultrasound waves by indwelling the capsule body unit 20 in the inner cavity of the subject P. In addition, the capsule body unit 20 can be easily inserted into the inner cavity of the subject P via the sheath 10.

In addition, the fixation mechanism 25 is provided at the outside position in the transmission and reception directions of ultrasound waves by the ultrasound transducer 21.

Thus, by arranging the fixation mechanism 25 on the outside in the transmission and reception directions of ultrasound waves, the transmission and reception of ultrasound waves are not prevented by the fixation mechanism 25. Therefore, the ultrasound medical apparatus can carry out the observation with ultrasound waves while being fixed by the fixation mechanism 25.

In addition, the fixation mechanism 25 according to the present embodiment includes the expansion unit 25a. The expansion unit 25a is provided in the capsule body unit 20, and expands by being supplied with a fluid from the outside. Further, the capsule body unit 20 can be fixedly arranged at the desired position in the sheath 10 (in the large diameter part 10b) by bringing the expanded expansion unit 25a into contact with the inner wall of the sheath 10 (the large diameter part 10b).

Specifically, a plurality of the expansion units 25a is arranged at the front and rear ends of the capsule body unit 20, while respective front end parts of the plurality of the expansion units 25a come into contact with the inner wall of the sheath 10.

Thus, the function of the fixation mechanism 25 can be fulfilled only when the capsule body unit 20 is fixedly arranged by providing the expansion unit 25a as the fixation mechanism 25. In addition, it is possible to fixedly arrange the capsule body unit 20 with greater certainty at the desired position in the sheath 10 by providing the plurality of the expansion units.

In addition, the ultrasound medical apparatus includes the cable unit 30. The cable unit 30 is flexible, as one end is coupled with the capsule body unit 20. The signal lines (the signal line SL1 and the signal line SL2) for transmitting and receiving signals between the capsule body unit 20 and the external device 40 and the fluid passage 60 for supplying a fluid to the expansion unit 25a from the external device 40 are arranged in the cable unit 30.

Thus, the transmission and reception of signals between the capsule body unit 20 and the external device 40 can be easily carried out by providing the cable unit 30. In addition, the wiring between the capsule body unit 20 and the external device 40 can be unified by providing the fluid passage 60 and the signal lines in one cable unit 30, allowing the ultrasound medical apparatus to be easily handled.

In addition, at least a part of the cable unit 30 has a structure such that the flexibility of which is lowered by being contorted.

The cable unit 30 can be formed into a paper-twisted shape by contorting the cable unit 30 having such the structure. Therefore, the capsule body unit 20 can be easily transferred in the sheath 10 by pushing and pulling the cable unit 30 by the operator.

In addition, the sheath 10 has a flat shape (for example, a rounded flat shape) with no liquid filled inside thereof.

Thus, the sheath 10 can be easily inserted into the inner cavity of the subject P by forming the sheath 10 into a flat shape.

In addition, the ultrasound diagnosis apparatus 1 including the ultrasound medical apparatus of the present embodiment can be also formed. The ultrasound diagnosis apparatus 1 includes the sheath 10, the capsule body unit 20, the fixation mechanism 25, the image generator 43, and the controller 44. The sheath 10 is inserted into the inner cavity of the subject P, and the outer peripheral surface of which (the outer peripheral surface of the large diameter part 10b) contacts the inner wall surface of the inner cavity of the subject P with a liquid filled inside thereof. The capsule body unit 20 is inserted in the sheath 10 (in the large diameter part 10b) to store the ultrasound transducer 21 that transmits and receives ultrasound waves to and from the subject P (the observation object in the subject P). The fixation mechanism 25 is provided in the capsule body unit 20 to fixedly arrange the capsule body unit 20 at a desired position in the sheath 10 (in the large diameter part 10b). The image generator 43 processes signals based on the reflected waves received by the ultrasound transducer 21, and generates image data. The controller 44 causes the display 45 to display the images based on the image data generated by the image generator 43.

Thus, the fixation mechanism 25 is provided to fixedly arrange the capsule body unit 20 at the desired position in the sheath 10 (in the large diameter part 10b). Therefore, the ultrasound diagnosis apparatus 1 of the present embodiment, it becomes possible to indwell the capsule body unit 20 capable of transmitting and receiving ultrasound waves in the observation object in the inner cavity of the subject P. Furthermore, the ultrasound diagnosis apparatus 1 can generate and display ultrasound images based on the echo signals acquired by the capsule body unit 20. As a result, it becomes possible to confirm and diagnose the state of the subject P when the operator, and the like, observes the observation object in the subject P.

It is assumed that the ultrasound diagnosis apparatus (ultrasound medical apparatus) according to the present embodiment is used in the following situations.

For example, the ultrasound diagnosis apparatus can be used for continuously monitoring the state of the heart H of the subject P hospitalized in the emergency medical department. Many of subjects P with acute cardiac disease and hospitalized in the emergency medical department are unconscious or cannot eat till treatment ends. Accordingly, even if the capsule body unit 20 is indwelled into the esophagus E, the subject P is less affected by discomfort, or the like.

Alternatively, the ultrasound diagnosis apparatus can be used even in situations without a specialist, for example, at an emergency medical site outside the hospital, and the like. Even in remote places, instructions for appropriate treatment can be obtained by transmitting the image data acquired through the ultrasound diagnosis apparatus to a large hospital where a specialist works. In addition, by transmitting the image data in advance from the emergency medical site to the hospital to which the subject is transferred, it becomes possible to transfer the subject with timely treatment upon arrival at the hospital. Furthermore, an ultrasound diagnosis apparatus as such can be downsized, therefore even at a location at which it is difficult to carry a dedicated large apparatus (a remote area, and the like), ultrasound diagnosis of the heart, or the like can be simply carried out.

Second Embodiment

Hereinafter, with reference to FIGS. 8A to 10, the ultrasound diagnosis apparatus 1 according to a second embodiment will be described. According to the present embodiment, an example in which a fastening unit 25c and an expansion unit 25d fixedly arrange the capsule body unit 20 at the desired position in the sheath 10 will be described. Detailed descriptions of structures identical with the first embodiment are sometimes omitted.

Figure 8A:
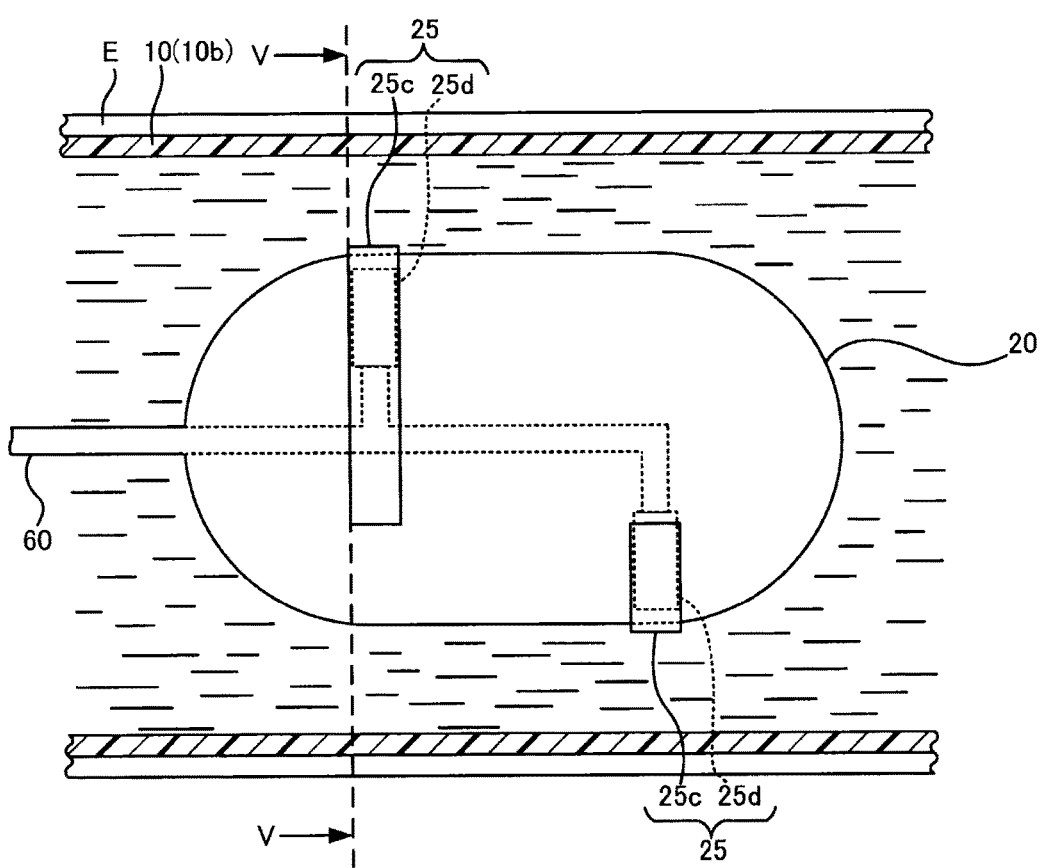
FIG. 8A is a view illustrating an example of the fixation mechanism according to a second embodiment.
Figure 8B:
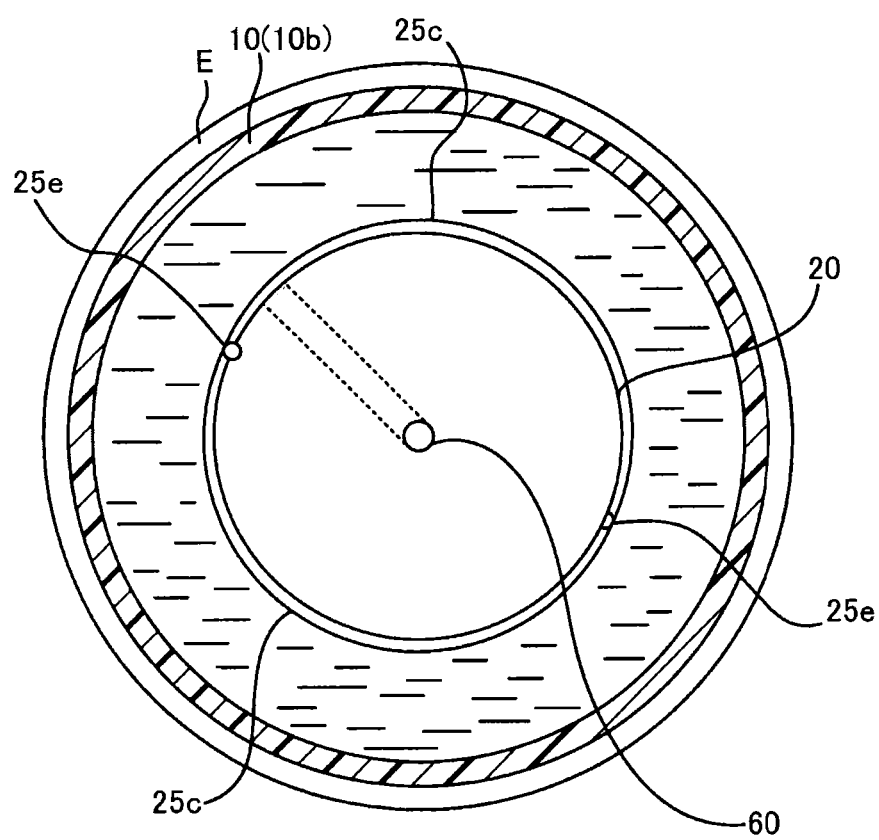
FIG. 8B is a view illustrating an example of the fixation mechanism according to a second embodiment.
Figure 8C:
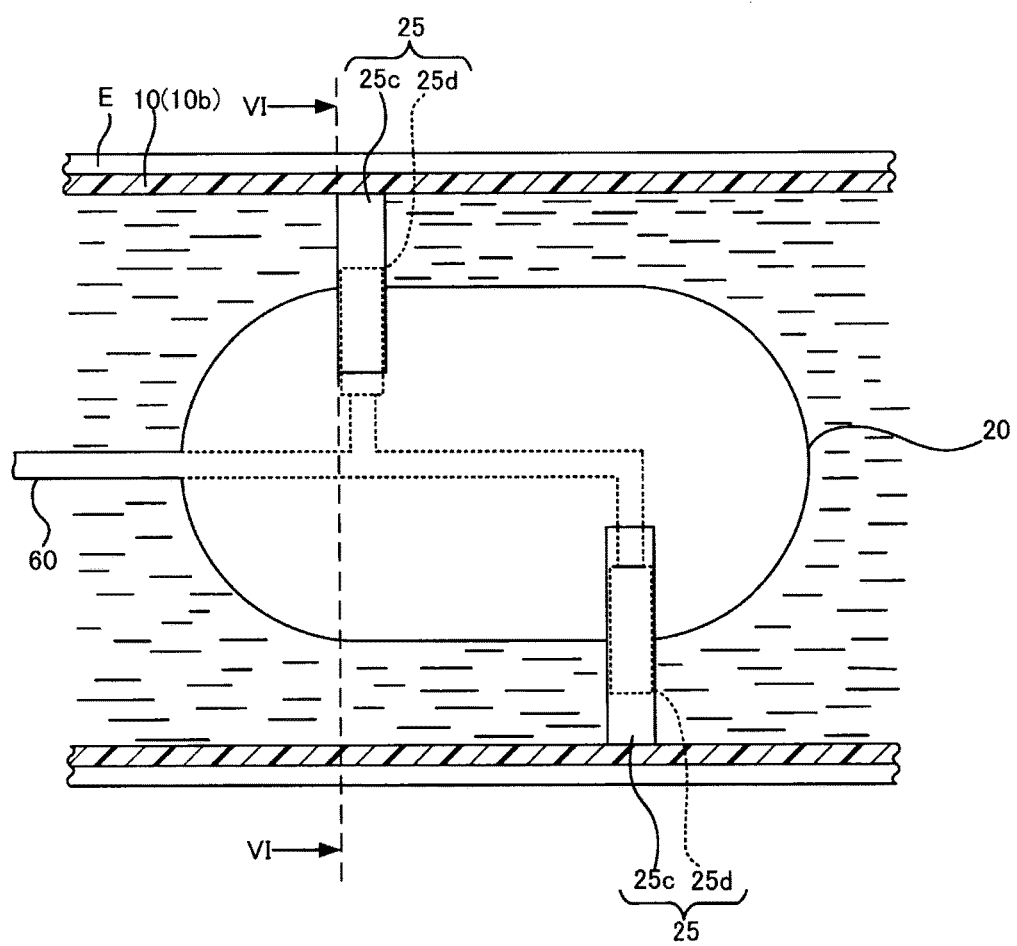
FIG. 8C is a view illustrating an example of the fixation mechanism according to a second embodiment.
Figure 8D:
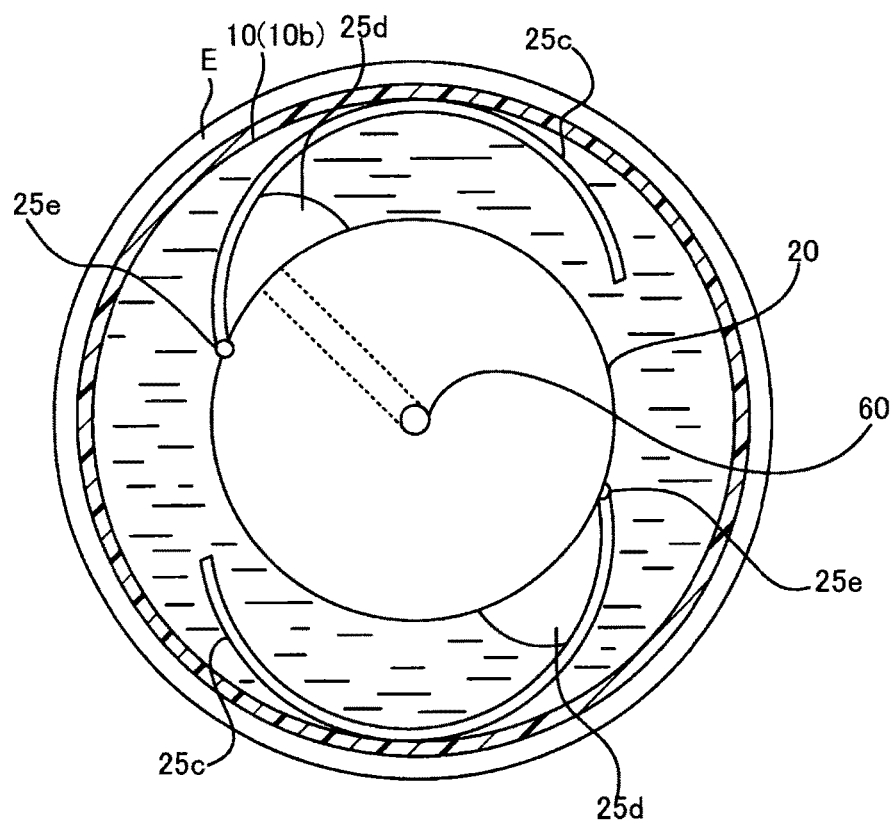
FIG. 8D is a view illustrating an example of the fixation mechanism according to a second embodiment.

The fixation mechanism 25 according to the present embodiment will be described in detail with reference to FIGS. 8A to 8D. FIGS. 8A and 8C are side views of the capsule body unit 20 inserted into the large diameter part 10b of the sheath 10. FIG. 8B is a section taken along direction V-V in FIG. 8A. FIG. 8D is a section taken along a direction VI-VI in FIG. 8C. Furthermore, in FIGS. 8A to 8D, illustrations of respective components stored in the capsule body unit 20 other than the fixation mechanism 25 and the cable unit 30 are omitted.

The fixation mechanism 25 according to the present embodiment includes the fastening unit 25c and the expansion unit 25d.

The fastening unit 25c arranged on the periphery of the capsule body unit 20 can be transferred in the radial direction of the capsule body unit 20. In the present embodiment, as illustrated in FIG. 8A, and the like, an example is illustrated in which two fastening units 25c are provided along the periphery of the capsule body unit 20. The fastening unit 25c can be transferred in the radial direction of the capsule body unit 20 around an axial part 25e (refer to FIG. 8B, and the like; the illustration is omitted in FIGS. 8A and 8C). The radial direction transferring means that a transfer vector has a radial direction component.

The fastening unit 25c is formed of an elastic member such as a resin material, or the like, or a less-elastic member such as a metallic material, or the like. In the case of forming the fastening unit 25c of a member that reflects and attenuates the ultrasound waves of a metallic material, and the like, the fastening unit 25c is preferably provided at a position outside in the transmission and reception directions of ultrasound waves.

The expansion unit 25d arranged between the fastening unit 25c and the capsule body unit 20 expands by being supplied with a fluid from the outside. In the present embodiment, as illustrated in FIG. 8D, the expansion unit 25d is arranged between the outer peripheral surface of the capsule body unit 20 and the fastening unit 25c. Further, as the expansion unit 25d is contracted in the state illustrated in FIG. 8B, illustration of the expansion unit is omitted.

The expansion unit 25d is communicated with the fluid passage 60. If a fluid is supplied from the external device 40 to the expansion unit 25d via the fluid passage 60, the expansion unit 25d expands. Due to the expansion of the expansion unit 25d, the fastening unit 25c is transferred in the radial direction. The transferred the fastening unit 25c comes into contact with the inner wall of the large diameter part 10b of the sheath 10 (refer to FIGS. 8C and 8D).

Thereby, it is possible to fixedly arrange the capsule body unit 20 at the desired position in the large diameter part 10b of the sheath 10 by expanding the expansion unit 25d via supply of the fluid and causing the fastening unit 25c to come into contact with the large diameter part 10b of the sheath 10.

Further, the structure of the fixation mechanism 25 according to the present embodiment is not limited to the above if the structure can fixedly arrange the capsule body unit 20 on the inner wall of the large diameter part 10b of the sheath 10 via the fastening unit by expanding the expansion unit 25d.

Figure 9A:
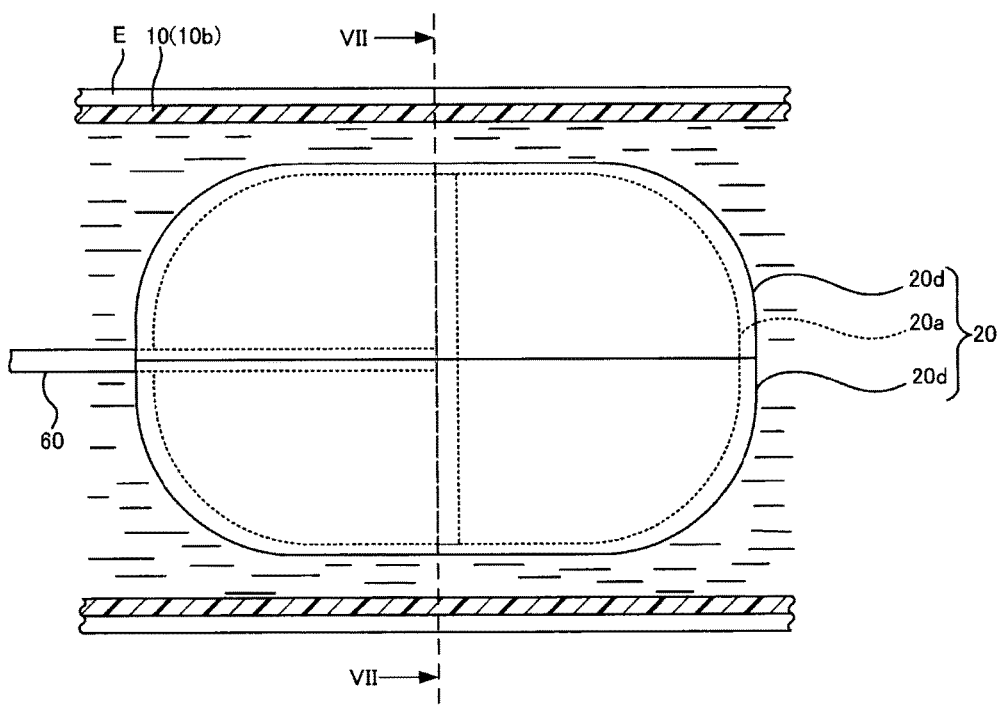
FIG. 9A is a view illustrating another example of the fixation mechanism according to the second embodiment.
Figure 9B:
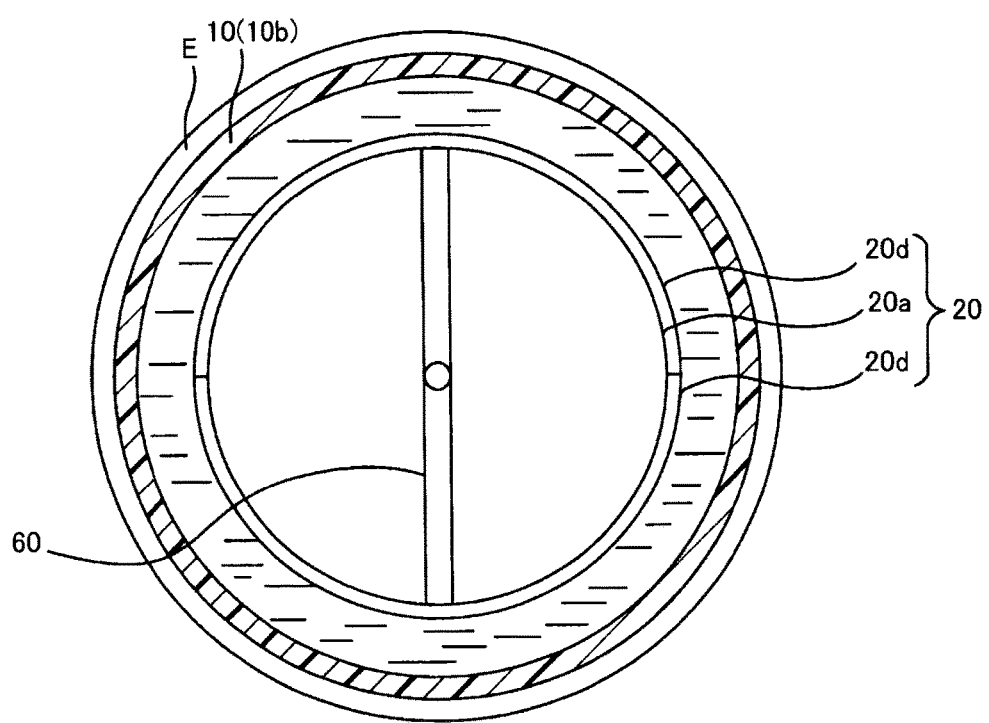
FIG. 9B is a view illustrating another example of the fixation mechanism according to the second embodiment.
Figure 9C:
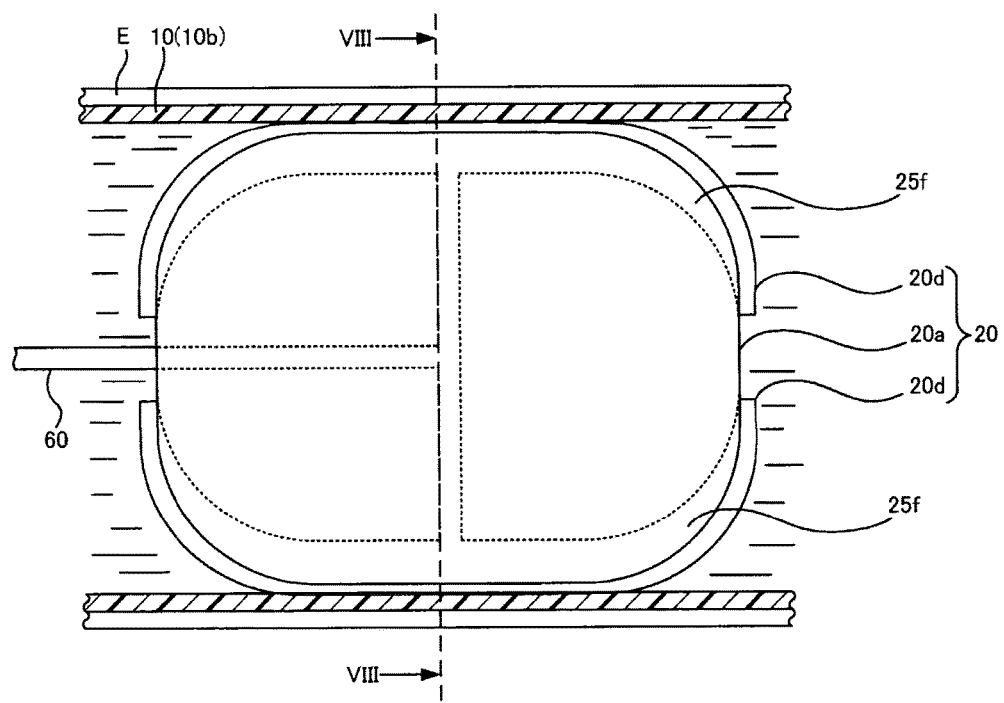
FIG. 9C is a view illustrating another example of the fixation mechanism according to the second embodiment.
Figure 9D:
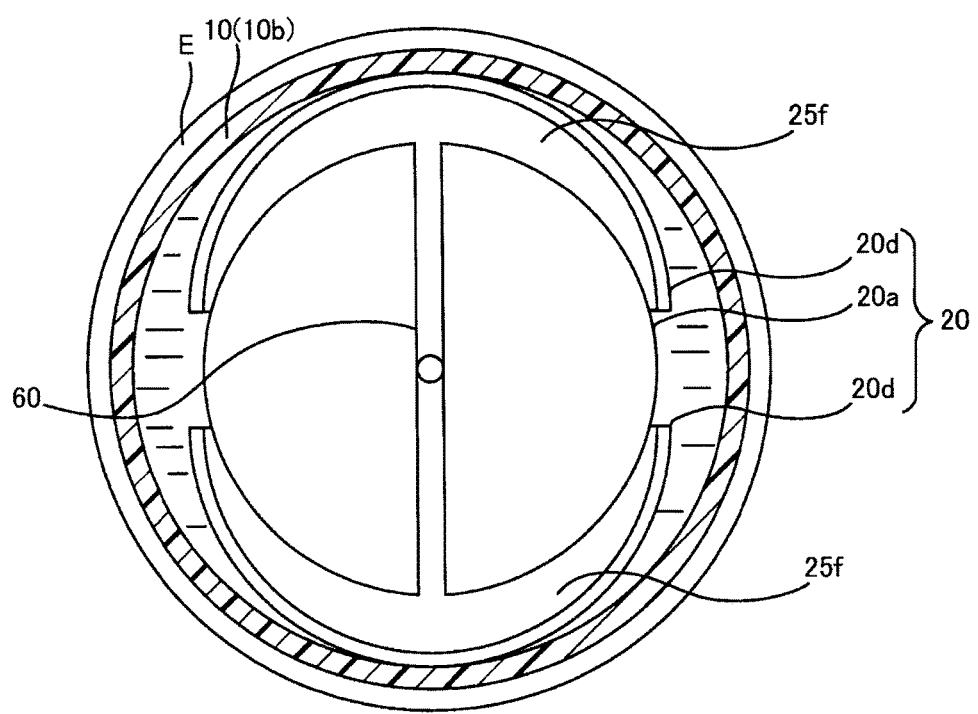
FIG. 9D is a view illustrating another example of the fixation mechanism according to the second embodiment.

Another example of the fixation mechanism 25 according to the present embodiment will be described with reference to FIGS. 9A to 9D. FIG. 9A and FIG. 9C are side views of the capsule body unit 20 inserted in the large diameter part 10b of the sheath 10. FIG. 9B is a sectional view taken along a direction VII-VII in FIG. 9A. FIG. 9D is a sectional view taken along a direction VIII-VIII in FIG. 9C. Furthermore, in FIGS. 9A to 9D, illustrations of respective components stored in the capsule body unit 20 other than the fixation mechanism 25 and the cable unit 30 are omitted.

The capsule body unit 20 illustrated in FIGS. 9A to 9D includes the main body part 20a and a shell part 20d. Respective components (other than the fixation mechanism 25) such as the ultrasound transducer 21, and the like, stored in the capsule body unit 20 are arranged in the main body part 20a. The shell part 20d is a hemisphere member to cover the main body part 20a, which is arranged in the radial direction of the main body part 20a in a transferable manner. In this example, two shell parts 20d are provided such that the parts 20d cover the main body part 20a (refer to FIG. 9A and the like)

An expansion unit 25f is arranged between the main body part 20a and the shell part 20d. The expansion unit 25f expands by being supplied with a fluid from the fluid passage 60. As illustrated in FIG. 9D, the expansion unit 25f is arranged between the main outer peripheral surface of the capsule body unit 20 and the shell part 20d. Further, as the expansion unit 25f is contracted in the state illustrated in FIGS. 9A and 9B, illustration thereof is omitted.

The shell part 20d transfers in the radial direction due to expansion of the expansion unit 25f. The transferred shell part 20d comes into contact with the inner wall of the large diameter part 10b of the sheath 10 (refer to FIGS. 9C and 9D). As a result, the shell part 20d can fixedly arrange the main body part 20a (the capsule body unit 20) at the desired position in the large diameter part 10b of the sheath 10. The shell part 20d of the present embodiment is an example of a "fastening unit." In addition, the shell part 20d and the expansion unit 25f form the fixation mechanism 25. Thus, the capsule body unit 20 can be downsized using a part of the capsule body unit 20, as a fastening unit.

Further, it is sufficient for a fastening unit and an expansion unit to be capable of fixedly arranging the capsule body unit 20 at the desired position in the large diameter part 10b of the sheath 10. In other words, the numbers, shapes, positions, and the like, of the fastening unit and the expansion unit are not limited to the above examples. For example, in the structure having the fastening unit 25c as illustrated in FIGS. 8A to 8D, it is also possible to provide a groove part into which the fastening unit 25c fits with the expansion unit 25d contracted on the outer peripheral surface of the capsule body unit 20. Due to such a structure, it is possible to decrease the external diameter of the capsule body unit 20, including the fixation mechanism 25. In other words, the capsule body unit 20 can be downsized.

<Operation>

The operation of the ultrasound diagnosis apparatus 1 according to the present embodiment will be described with reference to FIG. 10. Here, an example of observing the heart H by indwelling the capsule body unit 20 in the esophagus E will be described.

In the same manner as the first embodiment, the operator inserts the sheath 10 into the inner cavity of the subject P (S20). The controller 44 causes the liquid adjusting unit 48 to insert a liquid into the sheath 10 (S21). The sheath 10 injected with the liquid expands, while the outer peripheral surface of the large diameter part 10b contacts the inner wall surface of the esophagus E. The operator places the capsule body unit 20 into the sheath 10, and inserts the capsule body unit 20 into the desired position by pushing the cable unit 30 (S22). The controller 44 causes the fluid adjusting unit 49 to inject a fluid into the expansion unit 25f (S23).

The expansion unit 25d injected with the fluid expands to transfer the fastening unit 25c in the radial direction of the capsule body unit 20 (S24).

The fastening unit 25c comes into contact with the inner wall of the large diameter part 10b of the sheath 10, thereby fixedly arranging the capsule body unit 20 at the desired position in the large diameter part 10b of the sheath 10 (S25).

Subsequently, the observation with ultrasound waves is carried out by the capsule body unit 20 (S26).

Once the observation ends, the operator removes the sheath 10 and the capsule body unit 20 from the subject P (S27). Specifically, at first, the controller 44 causes the fluid adjusting unit 49 to evacuate the fluid in the expansion unit 25d. Due to evacuation of the fluid, the expansion unit 25d is contracted. The fastening unit 25c is separated from the inner wall of the large diameter part 10b of the sheath 10 by the contraction of the expansion unit 25d. In other words, the fixed arrangement of the capsule body unit 20 is released. Next, the controller 44 causes the liquid adjusting unit 48 to evacuate the liquid in the sheath 10. Due to evacuation of the liquid, the sheath 10 is contracted. In other words, the state in which the outer peripheral surface of the large diameter part 10b of the sheath 10 contacts the inner wall surface of the esophagus E is dissolved. As a result, it becomes possible to transfer the sheath 10 within the inner cavity of the subject P. It is possible to simultaneously remove the sheath 10 and the capsule body unit 20 from the subject P by pulling the opening part side of the sheath 10 together with the cable unit 30 with the capsule body unit 20 arranged in the sheath 10.

<Operation and Effect>

The operation and effect of the present embodiment will be described.

The fixation mechanism 25 according to the present embodiment includes the fastening unit 25c and the expansion unit 25d. The fastening unit 25c is arranged on the external peripheral of the capsule body unit 20, which can transfer in the radial direction of the capsule body unit 20. The expansion unit 25d is arranged between the fastening unit 25c and the capsule body unit 20, which expands by being supplied with a fluid from the outside. Further, the capsule body unit 20 can be fixedly arranged at the desired position in the large diameter part 10b of the sheath 10 when the expanded expansion unit 25d transfers the fastening unit 25c, allowing the fastening unit 25c to come into contact with the inner wall of the large diameter part 10b of the sheath 10.

Thus, it becomes also possible to indwell the capsule body unit 20 that can transmit and receive ultrasound waves into the observation object in the subject P by providing the fastening unit 25c and the expansion unit 25d as the fixation mechanism 25, in the same manner as the first embodiment.

Third Embodiment

Figure 12A:
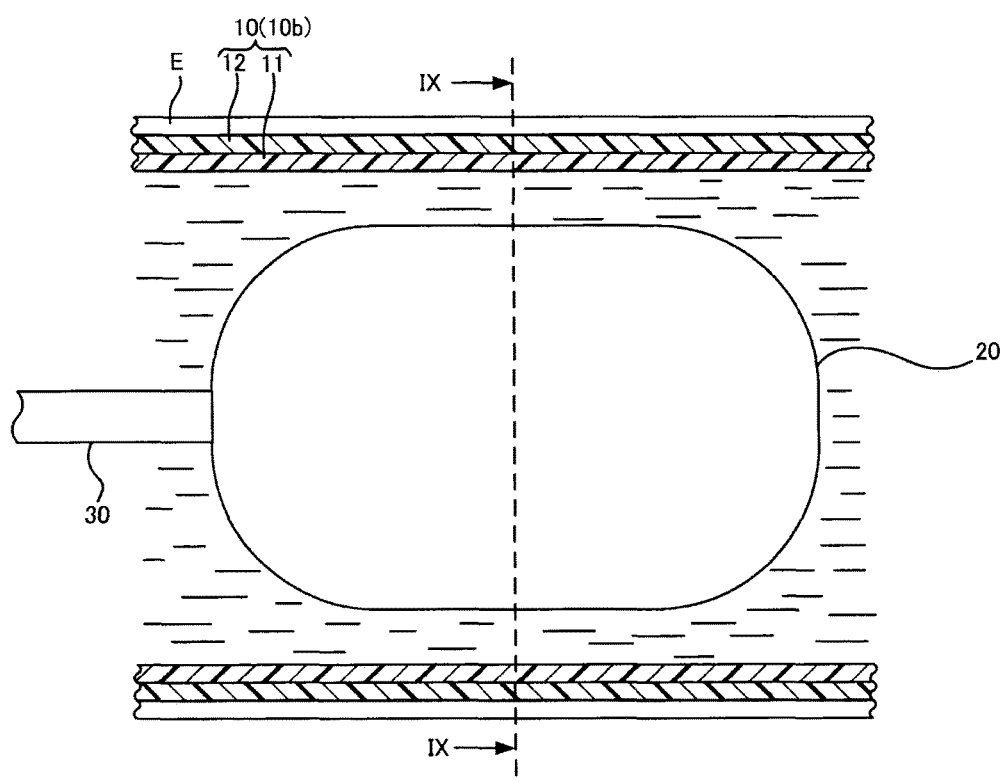
FIG. 12A is a view illustrating an example of the fixation mechanism according to the third embodiment.
Figure 12B:
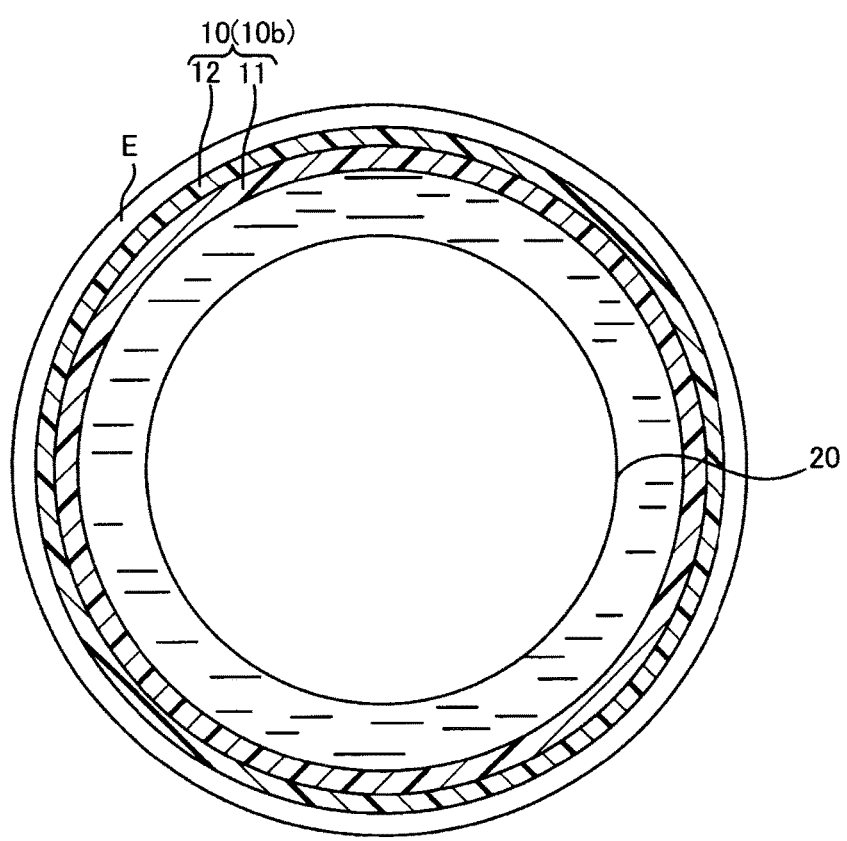
FIG. 12B is a view illustrating an example of the fixation mechanism according to the third embodiment.
Figure 12C:
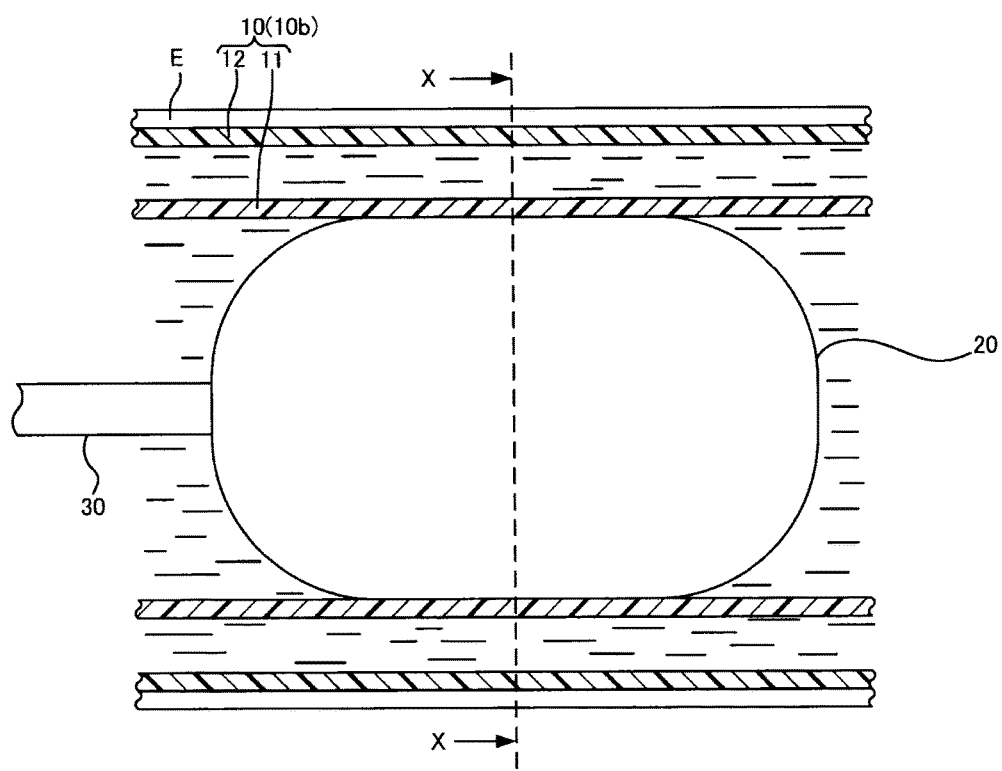
FIG. 12C is a view illustrating an example of the fixation mechanism according to the third embodiment.
Figure 12D:
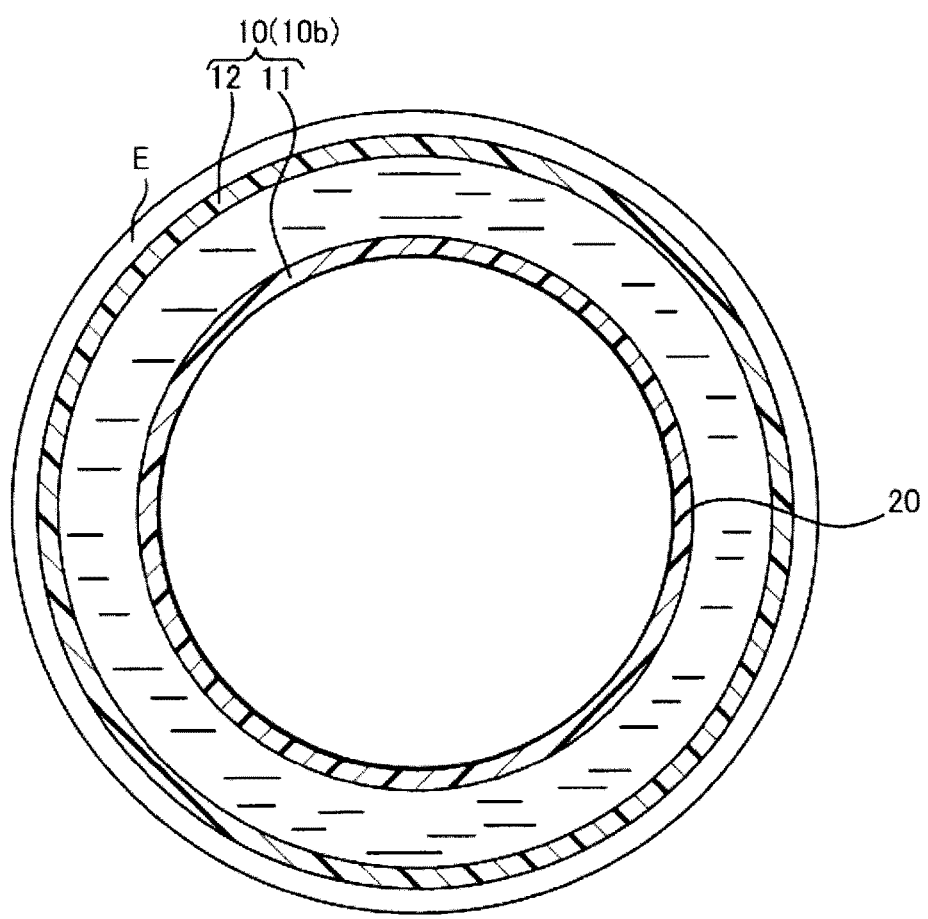
FIG. 12D is a view illustrating an example of the fixation mechanism according to the third embodiment.
Figure 13:
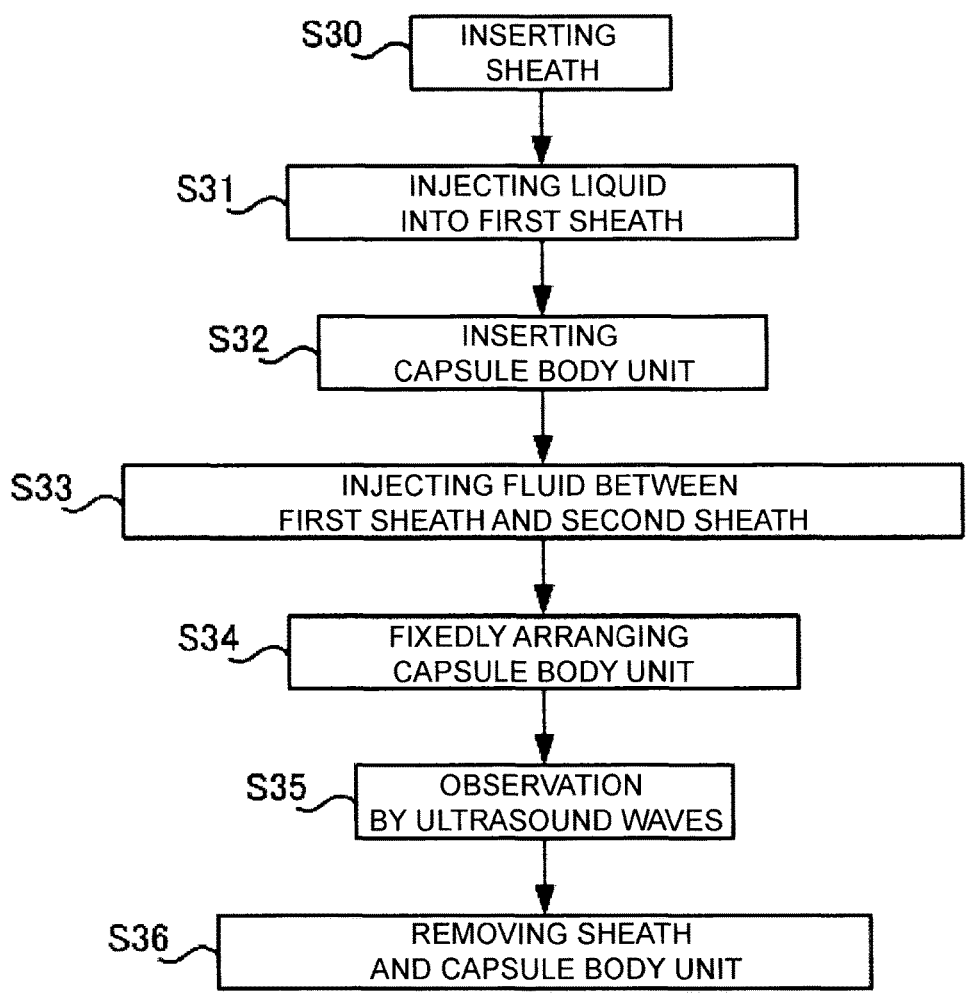
FIG. 13 is a flowchart illustrating the operation of the ultrasound diagnosis apparatus according to the third embodiment.

Hereinafter, with reference to FIGS. 11 to 13, the ultrasound diagnosis apparatus 1 according to a third embodiment will be described. According to the present embodiment, an example in which the fixation mechanism 25 is provided in the sheath 10 will be described. Detailed descriptions of structures identical with the first embodiment and the second embodiment are sometimes omitted.

FIG. 11 is a block diagram illustrating the structures of the capsule body unit 20 and the external device 40 according to the present embodiment. According to the present embodiment, the fixation mechanism 25 is arranged on the sheath 10 side. In addition, the liquid adjusting unit 48 in the external device 40 functions to inject and evacuate a liquid into and out of the sheath 10 (in a first sheath part 11, to be described later), and to inject and evacuate a liquid into and out of the fixation mechanism 25.

The fixation mechanism 25 according to the present embodiment will be described in detail with reference to FIGS. 12A to 12D. FIGS. 12A and 12C are side views of the capsule body unit 20 inserted into the large diameter part 10b of the sheath 10. FIG. 12B is a sectional view taken along a direction IX-IX in FIG. 12A. FIG. 12D is a sectional view taken along a direction X-X in FIG. 12C. Furthermore, in FIGS. 12A to 12D, illustrations of respective components stored in the capsule body unit 20 are omitted.

As illustrated in FIG. 12A, and the like, the sheath 10 (at least, the large diameter part 10b) of the present embodiment includes the first sheath part 11 and a second sheath part 12.

Each of the first sheath part 11 and the second sheath part 12 is a specific-length hollow member with an opening part formed at one end. Each of the first sheath part 11 and the second sheath part 12 is made of a material that can penetrate ultrasound waves.

In addition, the second sheath part 12 is provided such that the part 12 covers the first sheath part 11. In other words, the sheath 10 of the present embodiment has a double structure. Therefore, a liquid can be injected between the first sheath part 11 and the second sheath part 12 (the gap between the outer peripheral surface of the first sheath part 11 and the inner peripheral surface of the second sheath part 12). When the first sheath part 11 is filled with a liquid, the first sheath part 11 and the second sheath part 12 expand, the outer peripheral surface of the second sheath part 12 contacts the inner wall surface of the inner wall of the subject P (the esophagus E) (refer to FIGS. 12A and 12B). The capsule body unit 20 is inserted inside the first sheath part 11.

In the case of fixedly arranging the capsule body unit 20 at the desired position in the large diameter part 10b of the sheath 10 (in the first sheath part 11), the liquid adjusting unit 48 inserts a liquid between the first sheath part 11 and the second sheath part 12. In this case, as the second sheath part 12 contacts the inner wall surface of the esophagus E, the first sheath part 11 inwardly expands. The inner wall of the expanded first sheath part 11 comes into contact with the outer wall of the capsule body unit 20 inserted into the first sheath part 11 (refer to FIGS. 12C and 12D). Therefore, the capsule body unit 20 is fixedly arranged at the desired position in the first sheath part 11 (in the large diameter part 10b of the sheath 10).

The first sheath part 11 is an example of an "expansion unit." In addition, the first sheath part 11 and the second sheath part 12 form the fixation mechanism 25. Furthermore, the first sheath part 11 is preferably made of a material that is more elastic than the second sheath part 12. Such a structure makes it easier for the first sheath part 11 to inwardly expand when a liquid is injected between the first sheath part 11 and the second sheath part 12.

Furthermore, it is sufficient for the first sheath part 11 to be capable of fixedly arranging the capsule body unit 20 at the desired position in the first sheath part 11. In other words, the shape, and the like, of the first sheath part 11 are not limited to the above example. For example, the inner peripheral surface of the first sheath part 11 can be at least partly formed in a concavo-convex shape. In this case, since the capsule body unit 20 is securely fixed due to concavities and convexities, it is possible to fixedly arrange the capsule body unit 20 more securely in the first sheath part 11.

<Operation>

The operation of the ultrasound diagnosis apparatus 1 according to the present embodiment will be described with reference to FIG. 13. Here, an example of indwelling the capsule body unit 20 in the esophagus E to observe the heart H will be described.

The operator inserts the sheath 10 having the first sheath part 11 and the second sheath part 12 into the inner cavity of the subject P (S30).

The controller 44 causes the liquid adjusting unit 48 to inject a liquid into the first sheath part 11 (S31). Due to expansion of the first sheath part 11 filled with the liquid, the second sheath part 12 provided in the external peripheral of the first sheath part 11 also expands. As a result, the outer peripheral surface of the second sheath part 12 (outer peripheral surface of the large diameter part 10b of the second sheath part 12) contacts the inner wall surface of the esophagus E.

The operator places the capsule body unit 20 into the first sheath part 11, and inserts the capsule body unit 20 into the desired position by pushing the cable unit 30 (S32).

The controller 44 causes the liquid adjusting unit 48 to inject a liquid between the first sheath part 11 and the second sheath part 12 (S33).

Due to injection of the liquid, the first sheath part 11 inwardly expands. The capsule body unit 20 is fixedly arranged at the desired position in the large diameter part 10b of the sheath 10 when the inner wall of the first sheath part 11 (the large diameter part 10b of the first sheath part 11) comes into contact with the outer wall of the capsule body unit 20 (S34).

Subsequently, the capsule body unit 20 carries out the observation with ultrasound waves (S35).

Once the observation ends, the operator removes the sheath 10 and the capsule body unit 20 from the subject P (S36). Specifically, at first, the controller 44 causes the liquid adjusting unit 48 to evacuate the liquid between the first sheath part 11 and the second sheath part 12. Due to evacuation of the liquid, the first sheath part 11 is contracted. In other words, the fixed arrangement of the capsule body unit 20 is released. Next, the controller 44 causes the liquid adjusting unit 48 to evacuate the liquid in the first sheath part 11. Due to evacuation of the liquid, the sheath 10 is completely contracted. In other words, the state in which the outer peripheral surface of the large diameter part 10b of the second sheath part 12 contacts the inner wall surface of the esophagus E is dissolved. As a result, it becomes possible to transfer the sheath 10 within the inner cavity of the subject P. It is possible to simultaneously remove the sheath 10 and the capsule body unit 20 from the subject P by pulling the opening part side of the sheath 10 together with the cable unit 30 with the capsule body unit 20 arranged in the sheath 10.

Furthermore, the structures of the first embodiment, the second embodiment, and the third embodiment can also be combined. In other words, the fixation mechanism 25 may be provided in both the sheath 10 and the capsule body unit 20. In this case, it becomes possible to fixedly arrange the capsule body unit 20 more securely at the desired position in the sheath 10.

<Operation and Effect>

The operation and effect of the present embodiment will be described.

The fixation mechanism 25 according to the present embodiment includes an expansion unit (the first sheath part 11). The first sheath part 11 provided in the sheath 10 expands by being supplied with a liquid from the outside. Subsequently, it becomes possible to fixedly arrange the capsule body unit 20 at the desired position in the large diameter part 10b of the sheath 10 when the first sheath part 11 expands, allowing the inner wall of the first sheath part 11 to come into contact with the outer wall of the capsule body unit 20.

Thus, it becomes possible to indwell the capsule body unit 20 that can transmit and receive ultrasound waves in the observation object in the subject P by providing the fixation mechanism 25 on the sheath 10 side in the same manner as the first embodiment and the second embodiment. In addition, since the fixation mechanism 25 does not need to be provided on the capsule body unit 20, it becomes possible to downsize and simplify the capsule body unit 20.

Modified Example 1

For example, the inner wall surface of the actual the esophagus E has concavities and convexities. Accordingly, even if the sheath 10 is expanded by being filled with a liquid, it is possible that the outer peripheral surface of the sheath 10 may not sufficiently contact the inner wall surface of the esophagus E. Therefore, the sheath 10 is preferably structured such that adhesion between the outer peripheral surface and the inner wall surface of the subject P is enhanced.

Figure 14A:
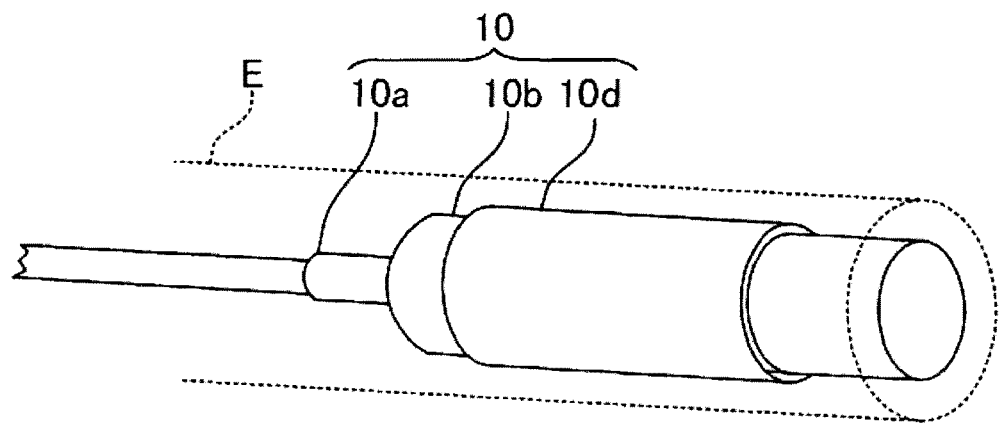
FIG. 14A is a view illustrating a sheath according to a modified example 1.
Figure 14B:
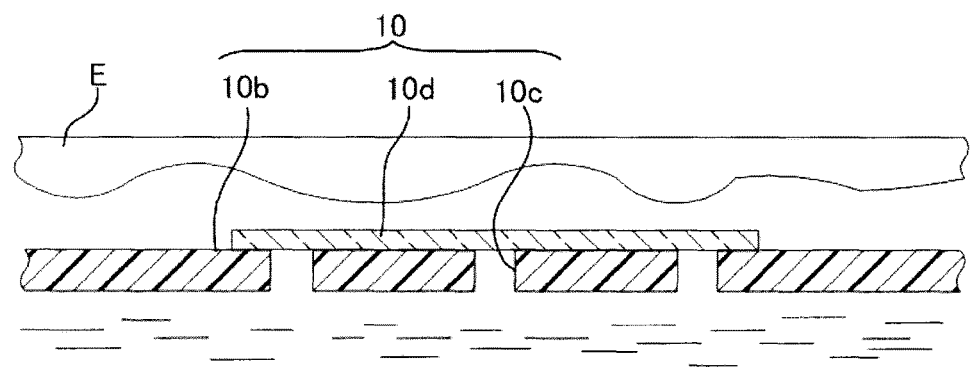
FIG. 14B is a view illustrating a sheath according to a modified example 1.
Figure 14C:
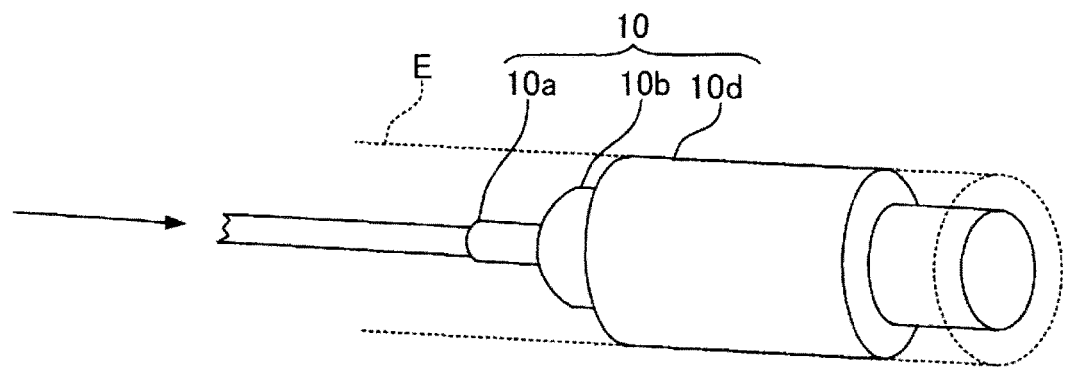
FIG. 14C is a view illustrating a sheath according to a modified example 1.
Figure 14D:
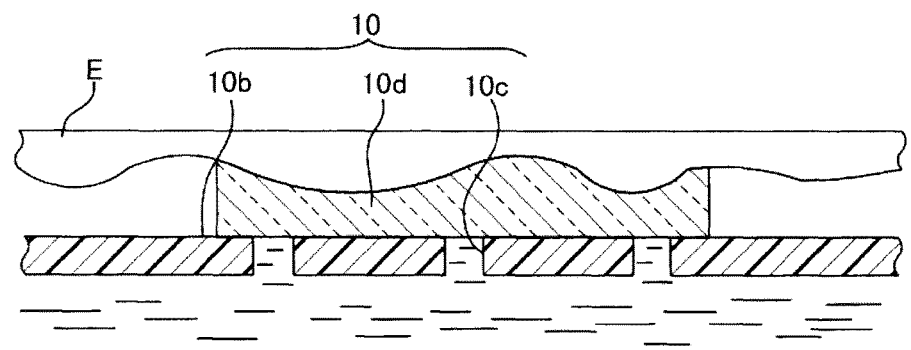
FIG. 14D is a view illustrating a sheath according to a modified example 1.

The structure of the sheath 10 according to the present modified example will be described with reference to FIGS. 14A to 14D. FIGS. 14A and 14C are perspective views schematically illustrating the sheath 10 according to the present modified example. FIGS. 14B and 14D are pattern views with the outer peripheral surface of the sheath 10 partly enlarged.

The sheath 10 includes micropores 10c and an absorbing member 10d.

The micropores 10c are formed at least partly on the outer peripheral surface of the sheath 10 (refer to FIG. 14B and the like). When a liquid is injected into the sheath 10 with the inner pressure of the sheath 10 raised, a liquid is exuded from the micropores 10c. FIG. 14B, and the like, illustrates the structure provided with a plurality of the micropores 10c; however, a single micropore 10c is sufficient.

The absorbing member 10d is a member provided at the position covering the micropores 10c. The absorbing member 10d generally formed in a thin sheet-like shape expands by absorbing a liquid, while it is made of a material that can penetrate ultrasound waves (a material that does neither reflect nor attenuate ultrasound waves).

The absorbing member 10d covering the micropores 10c expands by absorbing a liquid exuded from the micropores 10c, and comes into contact with the inner wall surface of the esophagus E as fitting to the shape thereof (refer to FIGS. 14C and 14D). Since the absorbing member 10d becomes more elastic than the sheath 10 by absorbing the liquid, adhesion with the inner wall surface of the esophagus E is improved.

Thus, by providing the micropores 10c and the absorbing member 10d in the sheath 10, even if the inner wall surface of the inner cavity of the subject P has concavities and convexities, it is possible to make the outer peripheral surface (the absorbing member 10d) of the sheath 10 come into secure contact with the inner wall surface of the inner cavity of the subject P.

Modified Example 2

During the observation by the ultrasound diagnosis apparatus 1, a large amount of echo signals are acquired. In other words, the amount of received data to be transmitted to the external device 40 also becomes large. In the present modified example, the structure of efficiently transmitting a large amount of received data based on the echo signals acquired by the capsule body unit 20 to the external device 40 will be described.

Figure 15:
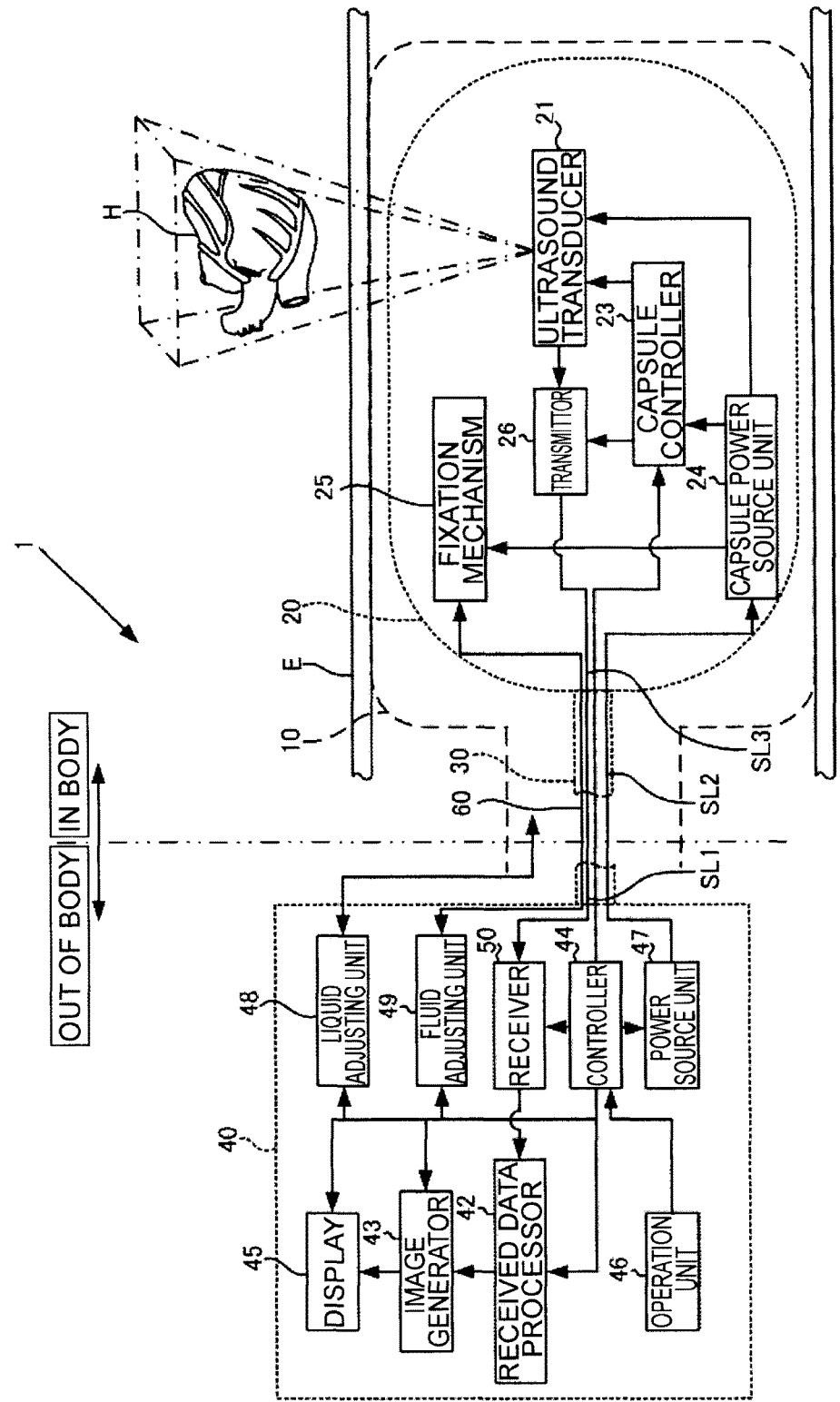
FIG. 15 is a block diagram illustrating the outline of the ultrasound diagnosis apparatus according to a modified example 2.

For example, as illustrated in FIG. 15, a transmitter 26 is provided in the capsule body unit 20. In addition, a receiver 50 is provided in the external device 40.

The transmitter 26 compresses the data amount by implementing compression-processing on the echo signals received by the ultrasound transducer 21. In addition, the transmitter 26 transmits the compressed received data to the receiver 50 provided to the external device 40 through a dedicated signal line SL3. The receiver 50 decompresses the compressed received data to output the decompressed data to the received data processor 42.

For data compression and decompression, publicly-known methods can be used. In addition, according to the present modified example, control signals, and the like, from the controller 44 are directly transmitted to the capsule controller 23 via the signal line SL1.

Thus, the transmitter 26 compression-processes the echo signals to transmit the signals to the external device 40 via the dedicated signal line SL3 as received data. In other words, according to ultrasound diagnosis apparatus of the present modified example, the data amount to be transmitted from the capsule body unit 20 to the external device 40 is reduced, enabling high-speed data transmission.

Alternatively, in the case of transmitting the data from the capsule body unit 20 to the external device 40, further high-speed data transmission can be carried out by converting the received data into image data rather than directly transmitting the received data. Therefore, the structure illustrated in FIG. 16 can also be employed as a structure for efficiently transmitting the received data.

According to the structure illustrated in FIG. 16, the received data processor 42 and the image generator 43 provided in the external device 40 of the abovementioned embodiments are provided in the capsule body unit 20. In FIG. 16, signal lines from the capsule controller 23 and the capsule power source unit 24 to respective components in the capsule body unit 20 are omitted.

The received data processor 42 according to the present modified example carries out signal processing directly on the echo signals based on the reflected waves received by the ultrasound transducer 21. The image generator 43 generates image data based on the signal-processed echo signals, and transmits the image data to the transmitter 26. The transmitter 26 transmits the image data to the receiver 50 of the external device 40 through the dedicated signal line SL3. The controller 44 causes the display 45 to display images based on the image data received by the receiver 50. Furthermore, the transmitter 26 may carry out compression processing on the image data. In this case, the receiver 50 decompresses the compressed image data.

Thereby, the capsule body unit 20 generates image data inside thereof to transmit the image data to the external device 40 via the dedicated signal line SL3. In other words, according to the ultrasound diagnosis apparatus 1 of the present modified example, high-speed data transmission becomes possible. In addition, real-time image data can be transmitted by forming the received data processor 42, the image generator 43, and the transmitter 26 from one semiconductor chip.

Modified Example 3

For example, during observation of the heart H, the capsule body unit 20 is sometimes arranged in the position at which the esophagus E has the largest diameter. Generally, the heart H is positioned diagonally to the position at which the esophagus E has the largest diameter. In other words, when the capsule body unit 20 is arranged in the position at which the esophagus E has the largest diameter, the capsule body unit 20 is positioned diagonally to the heart H. Accordingly, the capsule body unit 20 requires a structure that can diagonally transmit and receive ultrasound waves.

For example, as illustrated in FIG. 17, an angle change mechanism 27 is provided in the capsule body unit 20. The angle change mechanism 27 is arranged on the back surface of the ultrasound transducer 21, and holds the ultrasound transducer 21 such that the transducer 21 remains inclined at a specific angle. The specific angle can be predetermined by estimating the spatial position between the expected position at which the capsule body unit 20 is indwelled (for example, the position at which the esophagus E has the largest diameter) and the observation object (for example, the heart H). The ultrasound transducer 21 is enabled to transmit and receive ultrasound waves in the oblique direction while being held by the angle change mechanism 27.

Furthermore, depending on the body type and the age of the subject P, it is possible that the spatial position between the position at which the esophagus E has the largest diameter and the heart H differs. In addition, the operator sometimes desires to observe the heart H at a position other than the position at which the esophagus E has the largest diameter. Further, the operator sometimes desires to fine-adjust the transmission and reception directions of ultrasound waves with the capsule body unit 20 fixedly arranged in the sheath 10 by the fixation mechanism 25.

In this case, as illustrated in FIG. 18, the angle change mechanism 27 can be movably structured. The angle change mechanism 27 illustrated in FIG. 18 includes an opposed plate 27a and an adjusting mechanism 27b. The opposed plate 27a is a plate-like member provided on the back surface of the ultrasound transducer 21. The adjusting mechanism 27b is a mechanism which is provided on the back surface of the opposed plate 27a and changes the inclination of the ultrasound transducer 21 via the opposed plate 27a. The adjusting mechanism 27b is formed in an expandable and contractive shape (for example, an accordion structure). In the present modified example, the fluid adjusting unit 49 in the external device 40 is structured to inject and evacuate a fluid into and from the fixation mechanism 25 and the adjusting mechanism 27b. In FIG. 18, signal lines from the capsule power source unit 24 to respective components in the capsule body unit 20 are omitted.

The adjusting mechanism 27b extends and contracts when the fluid adjusting unit 49 injects and evacuates a fluid into and from the adjusting mechanism 27b. The inclination of the ultrasound transducer 21 is changed via the opposed plate 27a with expansion and contraction of the adjusting mechanism 27b. In other words, due to expansion and contraction of the adjusting mechanism 27b, it is possible to change the transmission and reception directions of ultrasound waves.

Furthermore, the adjusting mechanism 27b illustrated in FIG. 18 is structured to change inclination only uniaxially (inclination in the direction of the broken-line arrow in FIG. 18); however, it may be structured such that it is capable of changing inclination multiaxially. In addition, a motor can also be used as the adjusting mechanism 27b. The capsule controller 23 drives the opposed plate 27a by controlling the motor. In the case of using the motor as the adjusting mechanism 27b, a dedicated passage for injecting and evacuating a fluid from the fluid adjusting unit 49 becomes unnecessary.

Modified Example 4

For example, even for the case in which the capsule body unit 20 is fixedly arranged at the desired position in the large diameter part 10b of the sheath 10, there is the potential for the capsule body unit 20 to transfer due to the effect of peristalsis and respiration, or the like, of the esophagus E. In this case, the transmission and reception directions of ultrasound waves for the heart H are displaced. Therefore, ultrasound image data generated by the echo signals based on the received waves is also displaced. Thus, if the transmission and reception direction of ultrasound waves is displaced, inconvenience may be occurred in cases such as observing the heart H, and the like.

Therefore, according to the present modified example, as illustrated in FIG. 19, a displacement amount calculator 51 is provided in the external device 40, and a displacement correcting mechanism 28 is provided in the capsule body unit 20.

The displacement amount calculator 51 compares the image data acquired at a certain timing with the image data acquired at another timing to determine the presence or absence of displacement among images. For example, in the case of acquiring three-dimensional image data using a 2D array, the displacement amount calculator 51 calculates the displacement amounts in three-dimensional directions (XYZ direction), respectively. When it is determined that there is displacement among images, the displacement amount calculator 51 transmits the information about the displacement amounts to the capsule controller 23 via the transceiver 41.

The displacement correcting mechanism 28 is a mechanism for transferring the ultrasound transducer 21 in a specific direction (for example, the three-dimensional direction). When information regarding the displacement amount is transmitted from the displacement amount calculator 51, the capsule controller 23 causes the correcting mechanism 28 based on this information to transfer the ultrasound transducer 21 in a direction that dissolves displacement.

Furthermore, the method of correcting displacement is not limited to the abovementioned method alone and publicly-known methods can be also used. For example, the displacement amount calculator 51 compares the reference image data acquired in advance with the image data acquired at a different timing from that of the reference image data to calculate the displacement amount in the three-dimensional direction. The displacement amount calculator 51 transmits the calculated displacement amount to the image generator 43. The image generator 43 corrects the image data displacement acquired at different timings based on the transmitted displacement amount by the image processing. The controller 44 causes the display 45 to display images based on the corrected image data. In this case, the displacement correcting mechanism 28 becomes unnecessary.

Modified Example 5

According to the abovementioned embodiments, the structures of transmitting and receiving ultrasound waves using a 2D array as the ultrasound transducer 21 have been described; however, the structure of transmitting and receiving ultrasound waves in the capsule body unit 20 is not limited to this.

For example, as illustrated in FIG. 20, a structure in which two ultrasound transducers 21 are arranged in the capsule body unit 20 is possible. The resolution of images in the transmission direction of ultrasound waves is more often different from that in the vertical direction with respect thereto. Further, reflected waves of ultrasound waves have angle dependencies depending on the structure of the observation object (a valve of the heart H, and the like). If ultrasound waves vertically contacts the observation object, the reflected waves become strong, while if ultrasound waves obliquely contacts the observation object, the reflected waves become weak. Therefore, as the structure of arranging two ultrasound transducers 21, there is the possibility of generating image data in two directions for the same observation object, or, the possibility of generating higher-accuracy image data by synthesizing the echo signals thereof.

The respective ultrasound transducers 21 are inclined for the observation object (the heart H) by the angle change mechanism 27 such that the transmission directions of ultrasound waves overlap each other. In other words, the respective ultrasound transducers 21 can receive the reflected waves from different directions for the same observation object. The respective ultrasound transducers 21 control the transmission and reception of respective ultrasound waves to avoid overlapping each other. Furthermore, the two ultrasound transducers 21 can also receive the reflected waves of ultrasound waves transmitted from one of the ultrasound transducers 21. Due to the echo signals based on these reflected waves, the image generator 43 can manufacture image data in different directions for the same observation object. Alternatively, the image generator 43 can manufacture higher-accuracy image data by synthesizing these echo signals. In FIG. 20, the wiring between the capsule body unit 20 and the external device 40 (signal lines and the fluid passage 60) and signal lines from the capsule power source unit 24 to respective components in the capsule body unit 20 are omitted.

In addition, as the ultrasound transducer 21, a 1D array with transducer elements arranged in a line can also be used. In this case, a transfer mechanism (a transfer mechanism 29a, refer to FIG. 21A; a transfer mechanism 29b, refer to FIG. 22A) is provided in the capsule body unit 20. The transfer mechanism is a mechanism of transferring the 1D array in the arbitral direction. Even the ultrasound transducer of the 1D array can two-dimensionally or three-dimensionally transmit and receive ultrasound waves for the observation object by the transfer mechanism. Furthermore, in FIGS. 21A and 22A, the wiring between the capsule body unit 20 and the external device 40 (the signal lines and the fluid passage 60) and the signal lines from the capsule power source unit 24 to respective components in the capsule body unit 20 are omitted.

Figure 21B:
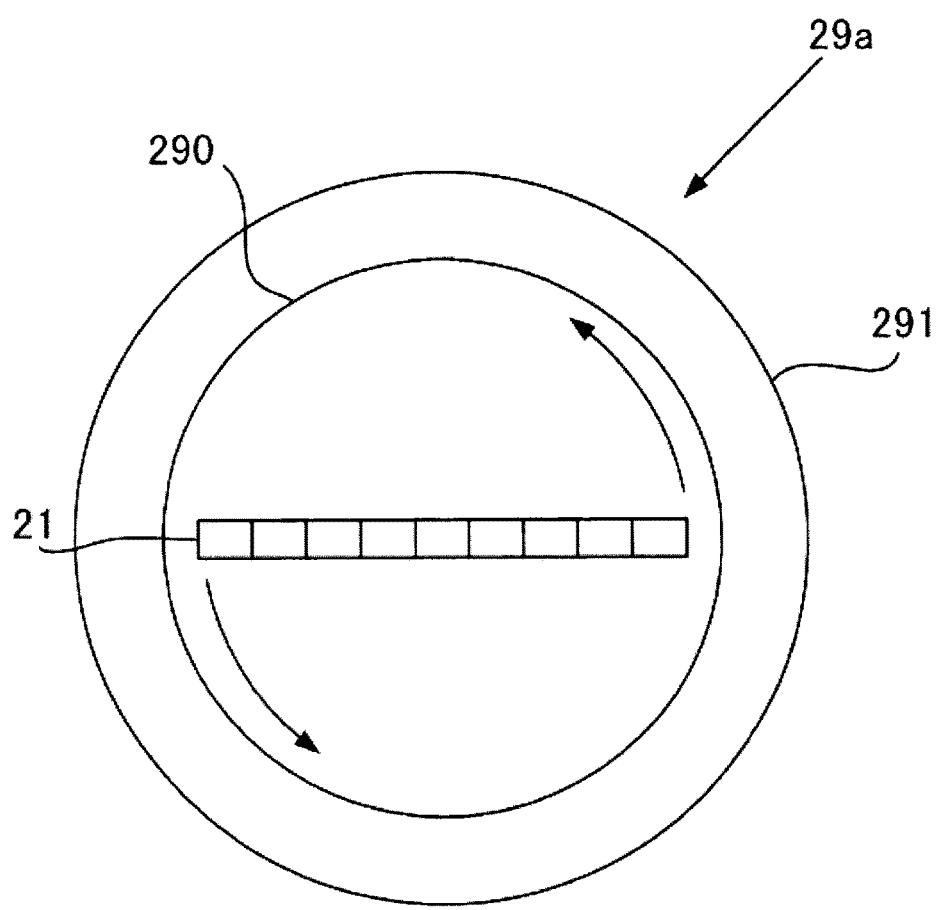
FIG. 21B is a view illustrating a transfer mechanism corresponding to FIG. 21A.

FIG. 21B illustrates an example of a specific structure of the transfer mechanism 29a. The transfer mechanism 29a includes a rotating part 290 and a fixing part 291. The 1D array (the ultrasound transducer 21) is arranged on the upper surface of the rotating part 290. The fixing part 291 is fixed in the capsule body unit 20 to rotatable hold the rotating part 290 (the arrows in FIG. 21B indicate the rotational direction of the rotating part 290).

The capsule controller 23 stops the rotating part 290 after rotating the part 290 by a specific transfer angle, and controls the ultrasound transducer 21 to transmit and receive ultrasound waves. The capsule controller 23 continuously repeats this control within the specific rotational range. In this case, the ultrasound transducer 21 can transmit and receive ultrasound waves in a three-dimensional domain formed in a conical shape (refer to FIG. 21A). Furthermore, if the transfer angle is decreased, it is possible to carry out transmission and reception of ultrasound waves with a high degree of accuracy in the three-dimensional domain formed in the conical shape. The echo signals based on the reflected waves received by the ultrasound transducer 21 are transmitted to the capsule transceiver 22 by a slip ring (not illustrated), or the like, via the fixing part 291.

The capsule controller 23 can arbitrarily control the rotational direction of the rotating part 290. For example, the capsule controller 23 can also control the rotating part to reciprocately rotate the ultrasound transducer 21, namely, to rotate the transducer in a certain direction by 180 degrees, and then rotate the transducer in the opposite direction by 180 degrees. In this case, the echo signals based on the reflective waves acquired by the rotating part 290 can be transmitted to the fixing part 291 using signal lines.

Figure 22A:
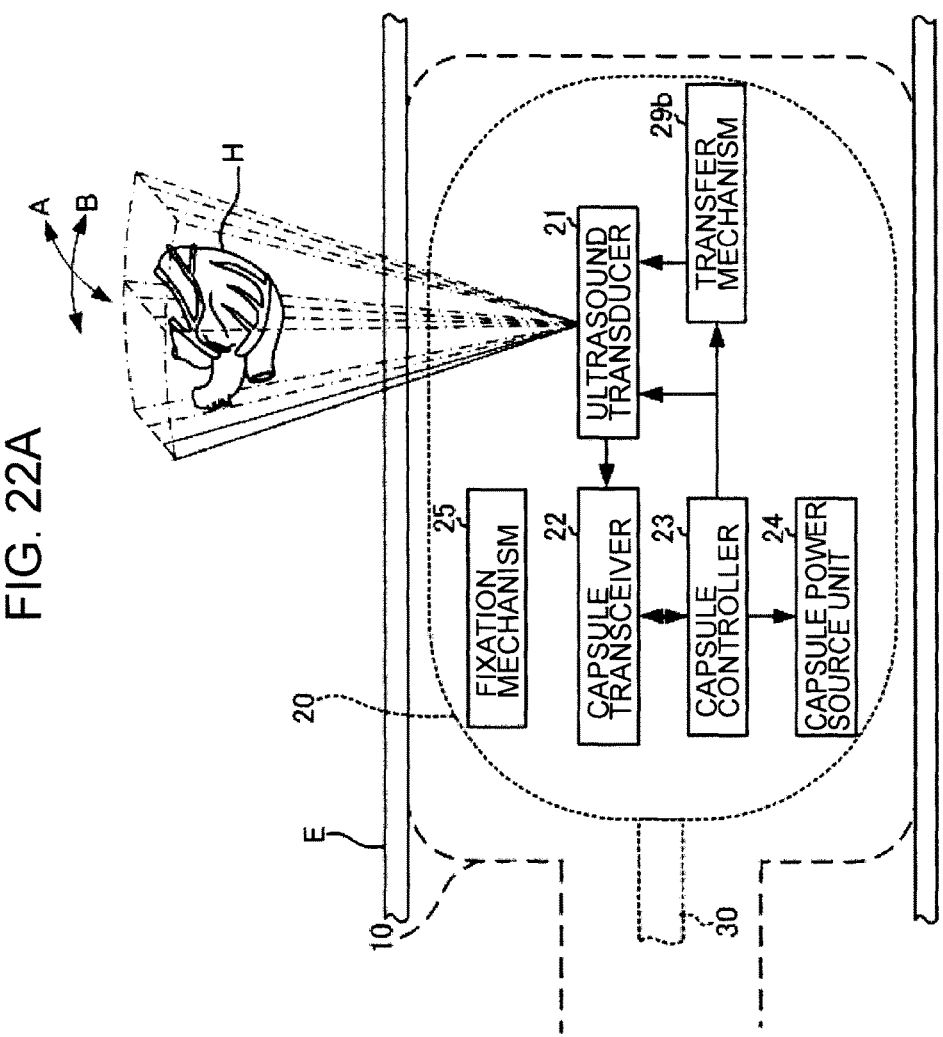
FIG. 22A is a block diagram illustrating another example of the capsule body unit according to the modified example 5.
Figure 22B:
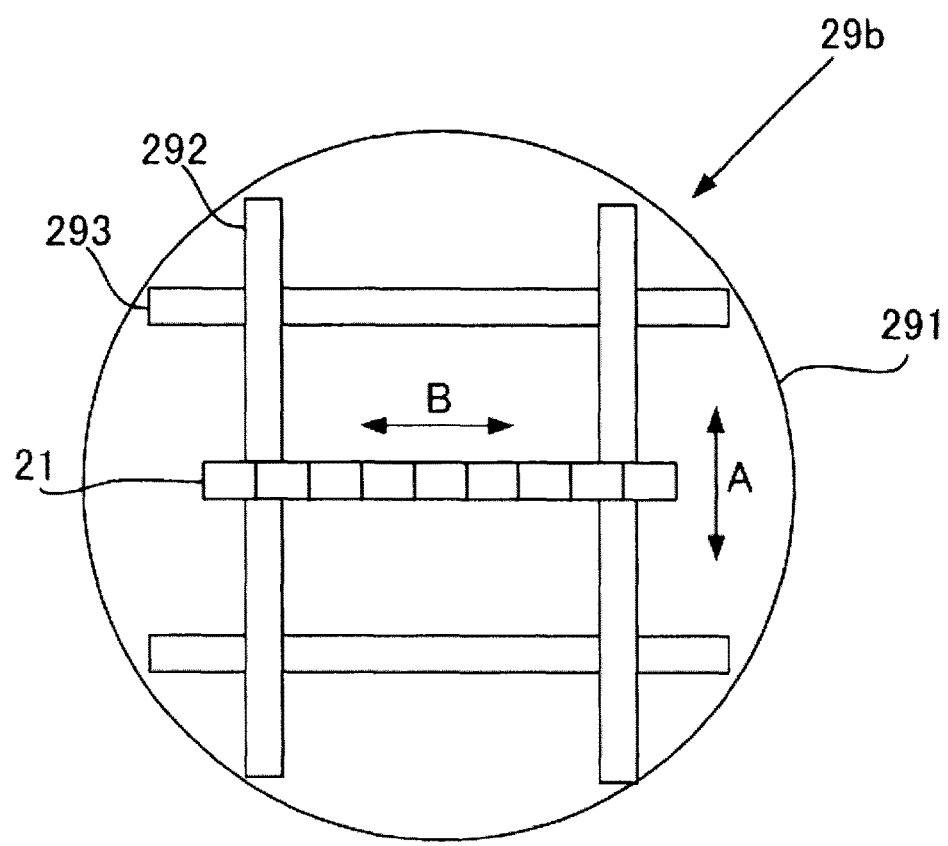
FIG. 22B is a view illustrating the transfer mechanism corresponding to FIG. 22A.

FIG. 22B illustrates an example of a specific structure of the transfer mechanism 29b. The transfer mechanism 29b includes the fixing part 291, a slide part 292, and a slide part 293.

The slide part 292 is formed of a pair of members, in which the ultrasound transducer 21 is arranged. The slide part 292 is a mechanism of transferring the ultrasound transducer 21 in a specific direction (a direction of an arrow A in FIG. 22B). The slide part 293 is formed of a pair of members, on which the slide part 292 is arranged. The slide part 293 is a mechanism for transferring the ultrasound transducer 21 in the direction perpendicular to the specific direction (the direction A) (a direction of an arrow B in FIG. 22B) via the slide part 292. The slide part 293 is fixed on the fixing part 291. A stepping motor can be used as the slide part 292 and the slide part 293.

The capsule controller 23 causes the slide part 292 and the slide part 293 respectively to stop after driving a specific transfer amount, and controls the ultrasound transducer 21 to transmit and receive ultrasound waves. The capsule controller 23 continuously repeats this control within a specific transfer range. In this case, the ultrasound transducer 21 can transmit and receive ultrasound waves in a three-dimensional domain formed in a quadrangular pyramid composed of plural two-dimensional domains (refer to FIG. 22A). Further, if the transfer amounts of the respective slide parts are decreased, it is possible to carry out the transmission and reception of ultrasound waves with a high degree of accuracy in the three-dimensional domain formed in the quadrangular pyramid. In FIG. 22A, the domain represented by solid lines extending from the ultrasound transducer 21 indicates a two-dimensional domain (a single two-dimensional domain) in which ultrasound waves are transmitted and received with the ultrasound transducer 21 arranged at a certain position. When the capsule controller 23 drives the slide part 292 and the slide part 293, the ultrasound transducer 21 can transmit and receive ultrasound waves for the entire domain represented by dashed-dotted lines in FIG. 22A.

Furthermore, in the case of transferring the ultrasound transducer 21 in only one direction, it is sufficient if any one of the slide part 292 and the slide part 293 is provided. In addition, by forming the slide part 292 and the slide part 293 in an arc-like shape, the transfer range of the ultrasound transducer 21 can be broadened. The transmission and reception range of ultrasound waves can be broadened by transferring the ultrasound transducer 21 over a broad range. Further, the slide part 292 and the slide part 293 are not limited to the stepping motor. For example, the slide part 292 and the slide part 293 can be structured as a mechanism for transferring the ultrasound transducer 21 due to the injection and evacuation of a fluid into and from the fluid adjusting unit 49.

Modified Example 6

The entire structure of the ultrasound diagnosis apparatus 1 (ultrasound medical apparatus) is not limited to the above-mentioned example.

Figure 23:
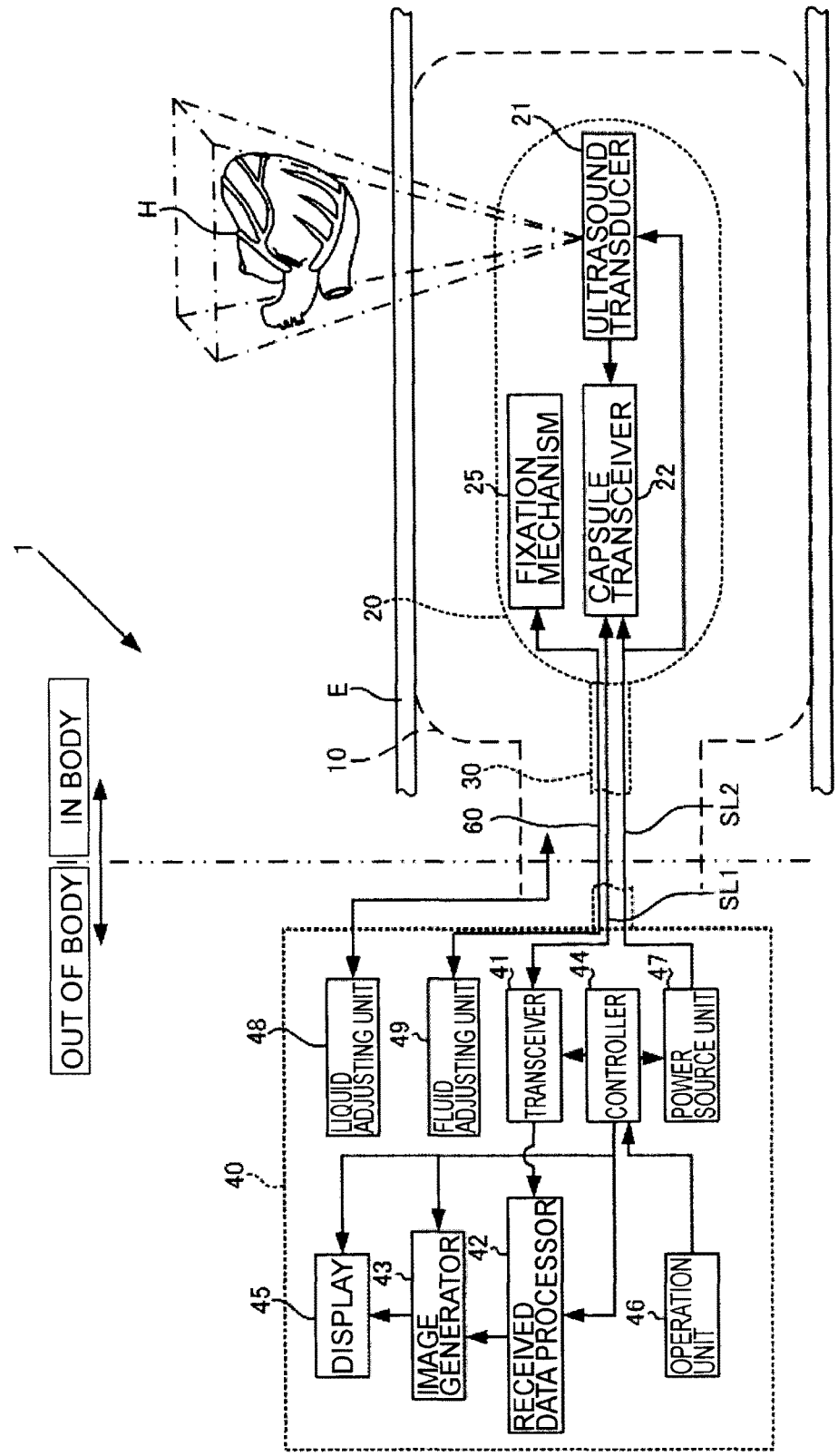
FIG. 23 is a block diagram illustrating the outline of the ultrasound diagnosis apparatus according to a modified example 6.

For example, as illustrated in FIG. 23, the structure of arranging only the ultrasound transducer 21, the capsule transceiver 22, and the fixation mechanism 25 in the capsule body unit 20 is also available. In this case, the controller 44 of the external device 40 controls the respective components in the capsule body unit 20 via the transceiver 41 to drive the ultrasound transducer 21, and the like. In addition, the power source unit 47 transmits electric power to drive the respective components in the capsule body unit 20 via the signal line SL2. Due to the employment of such the structure, the structures of the capsule controller 23 and the capsule power source unit 24 become unnecessary. Accordingly, downsizing of the capsule body unit 20 can be conducted.

Furthermore, it is possible to provide a battery, or the like, in the capsule body unit 20 as a power source of the capsule body unit 20. In this case, as it is not necessary to supply power from the external device 40 to the capsule body unit 20, the signal line SL2 becomes unnecessary. Therefore, the diameter of the cable unit 30 can be made thin.

Figure 24:
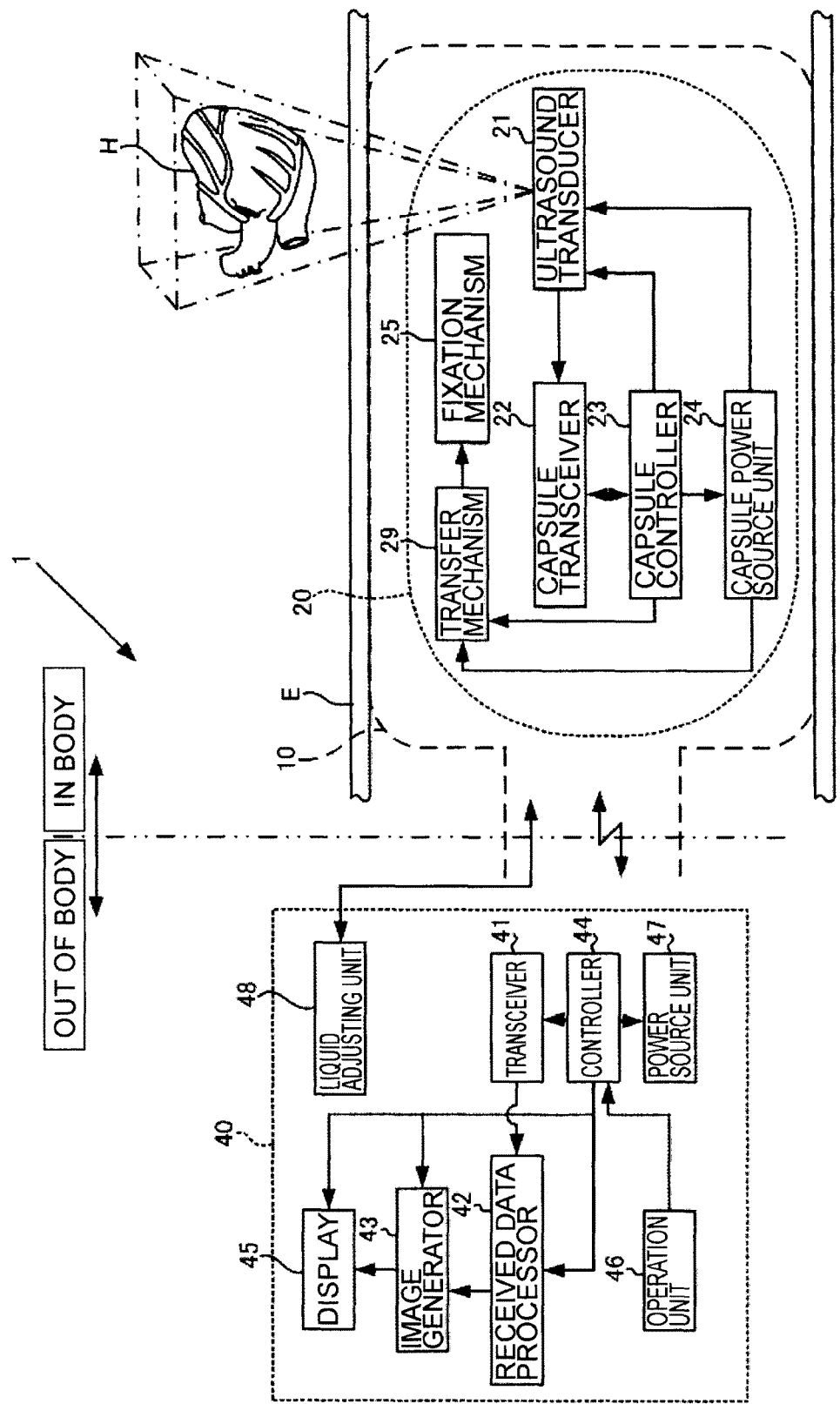
FIG. 24 is a block diagram illustrating another example of the ultrasound diagnosis apparatus according to the modified example 6.

Alternatively, as illustrated in FIG. 24, it is also possible to wirelessly communicate transmission and reception of signals and electricity supply between the external device 40 and the capsule body unit 20. The transmission and reception of various signals can use the methods of publicly-known wireless communication and wireless power supply. In this case, the signal line SL1 and the signal line SL2 become unnecessary. Further, the ultrasound diagnosis apparatus 1 illustrated in FIG. 24 includes a capsule fluid adjusting unit 29 in the capsule body unit 20. The capsule fluid adjusting unit 29 injects and evacuates a fluid into and from the fixation mechanism 25 based on control of the capsule controller 23. For example, the fluid is supplied from the surrounding of the capsule body unit 20. Furthermore, the fluid evacuated from the fixation mechanism 25 can be released to the surrounding of the capsule body unit 20. In this case, as the fluid passage 60 also becomes unnecessary, the cable unit 30 itself becomes unnecessary. Accordingly, for example, even in the case of indwelling the capsule body unit 20 of the subject P in a conscious state, the cable unit 30 does not extend from the oral cavity. Therefore, it becomes possible to reduce the discomfort of the subject P during the use of the ultrasound diagnosis apparatus 1.

Modified Example 7

Figure 25:
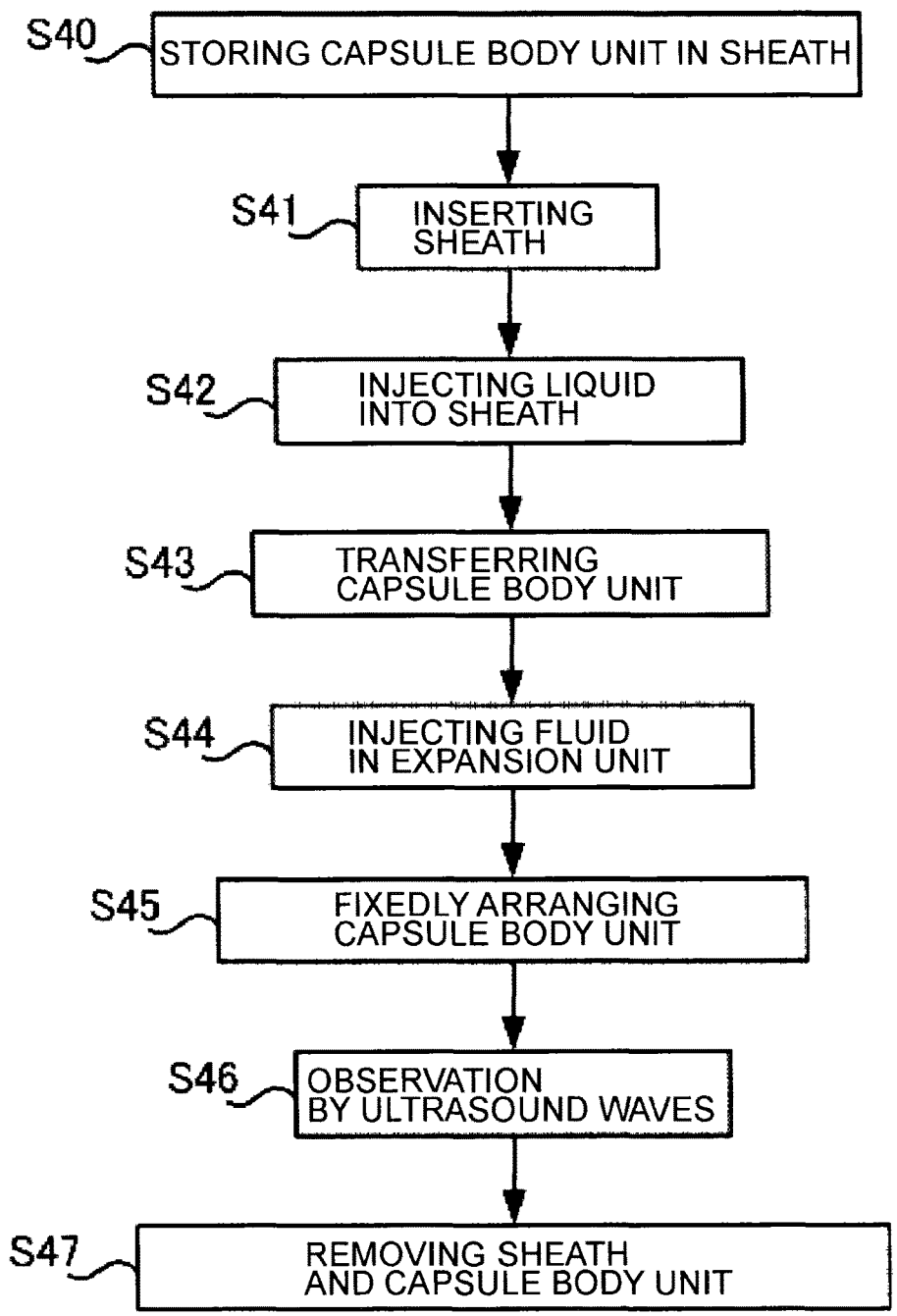
FIG. 25 is a flowchart illustrating the operation of the ultrasound diagnosis apparatus according to a modified example 7.

The method of inserting the capsule body unit 20 and the sheath 10 into the inner cavity of the subject P also includes the following example. FIG. 25 is a flowchart illustrating the operation of the ultrasound diagnosis apparatus 1 according to the present modified example. FIG. 25 explains the present modified example based on the structure of the first embodiment.

At first, the capsule body unit 20 is stored in advance in the sheath 10 (in the large diameter part 10*b*) folded in a flat shape (S40).

Subsequently, the operator inserts the sheath 10 having the capsule body unit 20 stored in the inner cavity of the subject P (S41).

The controller 44 causes the liquid adjusting unit 48 to inject a liquid into the sheath 10 (S42).

The operator transfers the capsule body unit 20 to a desired position by pushing the cable unit 30 (S43).

The controller 44 causes the fluid adjusting unit 49 to inject a fluid in the expansion unit 25*a* (S44).

The expansion unit 25*a* injected with the fluid expands to come into contact with the inner wall of the large diameter part 10*b* of the sheath 10, thereby fixedly arranging the capsule body unit 20 at the desired position in the large diameter part 10*b* of the sheath 10 (S45).

Subsequently, the observation with ultrasound waves is carried out by the capsule body unit 20 (S46).

Once the observation ends, the operator removes the sheath 10 and the capsule body unit 20 from the subject P (S47).

Thus, by storing the capsule body unit 20 in the sheath 10 in advance, even an operator unfamiliar with the procedures can easily carry out the procedures.

Common Effects in the Embodiments

According to the ultrasound medical apparatus of at least one of the abovementioned embodiments, due to the fixation mechanism provided in at least one of the capsule body unit and the sheath, it is possible to fixedly arrange the capsule body unit at a desired position in the sheath. Accordingly, it is possible to indwell the capsule body unit at the desired position in the sheath for the observation object.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound medical apparatus, comprising:
   a sheath, inserted into the inner cavity of a subject, having an outer peripheral surface that contacts the inner wall surface of the inner cavity of the subject with a liquid filled inside thereof;
   a capsule body unit inserted into the sheath, having a capsule-shaped outer periphery so as to pass through a throat, and including a main body part configured to store an ultrasound transducer that transmits and receives ultrasound waves to and from the subject; and
   a fixation mechanism provided in at least one of the capsule body unit and the sheath, and configured to fixedly arrange the capsule body unit at a desired position in the sheath, wherein
   the capsule body unit is transferable in an insertion direction and an opposite direction thereof in the sheath.

2. The ultrasound medical apparatus according to claim 1, wherein the fixation mechanism is provided on the outside in the transmission and reception directions of ultrasound waves by the ultrasound transducer so as not to interfere with transmission and reception of ultrasound waves.

3. The ultrasound medical apparatus according to claim 1, wherein the fixation mechanism comprises an expansion unit provided on the capsule body unit, which expands by being supplied with a fluid from outside, wherein
   the fixation mechanism is a mechanism configured to fixedly arrange the capsule body unit at the desired position in the sheath by making the expanded expansion unit come into contact with the inner wall of the sheath.

4. The ultrasound medical apparatus according to claim 3, wherein a plurality of the expansion units are arranged at the front end and/or rear end of the capsule body unit, while the respective front end parts of the plurality of the expansion units come into contact with the inner wall of the sheath.

5. The ultrasound medical apparatus according to claim 1, wherein the fixation mechanism comprises:
   a fastening unit arranged on the external peripheral of the capsule body unit, and configured to be transferable in the radial direction of the capsule body unit; and
   an expansion unit arranged between the fastening unit and the capsule body unit, which expands by being supplied with a fluid from outside, wherein
   the fixation mechanism is a mechanism configured to fixedly arrange the capsule body unit at the desired position in the sheath when the expansion unit expands and transfers the fastening unit in the radial direction, and the fastening unit comes into contact with the inner wall of the sheath.

6. The ultrasound medical apparatus according to claim 1, wherein the fixation mechanism comprises an expansion unit arranged in the sheath, which expands by being supplied with a liquid from outside, wherein the fixation mechanism is a mechanism configured to fixedly arrange the capsule body unit at the desired position in the sheath when the expansion unit expands and the inner wall of the expansion unit comes into contact with the outer wall of the capsule body unit.

7. The ultrasound medical apparatus according to claim 3, comprising a cable unit having flexibility, wherein one end is coupled to the capsule body unit, wherein a signal line configured to transmit and receive signals between the capsule body unit and an external device and a fluid passage configured to supply a fluid to the expansion unit from the external device are arranged in the cable unit.

8. The ultrasound medical apparatus according to claim 7, wherein at least a part of the cable unit comprises a structure in which the flexibility thereof is lowered by being contorted.

9. The ultrasound medical apparatus according to claim 1, wherein the sheath has a flat shape in a state that no liquid filled inside thereof.

10. The ultrasound medical apparatus, according to claim 1, wherein the sheath, comprises:

micropores formed on at least a part of the outer peripheral surface; and an absorbing member provided at the position covering the micropores that expands by absorbing the liquid flowing out of the micropores to come into contact with the inner wall surface of the subject.

11. The ultrasound medical apparatus according to claim 2, wherein the fixation mechanism comprises an expansion unit provided on the capsule body unit, which expands by being supplied with a fluid from outside, wherein the fixation mechanism is a mechanism configured to fixedly arrange the capsule body unit at the desired position in the sheath by making the expanded expansion unit come into contact with the inner wall of the sheath.

12. The ultrasound medical apparatus according to claim 11, wherein a plurality of the expansion units are arranged at the front end and/or rear end of the capsule body unit, while the respective front end parts of the plurality of the expansion units come into contact with the inner wall of the sheath.

13. The ultrasound medical apparatus according to claim 2, wherein the fixation mechanism comprises:

a fastening unit arranged on the external peripheral of the capsule body unit, and configured to be transferable in the radial direction of the capsule body unit; and an expansion unit arranged between the fastening unit and the capsule body unit, which expands by being supplied with a fluid from outside, wherein the fixation mechanism is a mechanism configured to fixedly arrange the capsule body unit at the desired position in the sheath when the expansion unit expands and transfers the fastening unit in the radial direction, and the fastening unit comes into contact with the inner wall of the sheath.

14. An ultrasound diagnosis apparatus, comprising:

a sheath inserted into the inner cavity of a subject having the outer peripheral surface contacts the inner wall surface of the inner cavity of the subject with a liquid filled inside thereof;

a capsule body unit inserted into the sheath, having a capsule-shaped outer periphery so as to pass through a throat, and including a main body part configured to store an ultrasound transducer that transmits and receives ultrasound waves to and from the subject;

a fixation mechanism provided in at least one of the capsule body unit and the sheath, and configured to fixedly arrange the capsule body unit at a desired position in the sheath;

an image generator configured to process signals based on the reflected waves received by the ultrasound transducer to generate image data; and a controller configured to cause a display to display the images based on the image data generated by the image generator, wherein the capsule body unit is transferable in an insertion direction and an opposite direction thereof in the sheath.

* * * * *